US009855150B2

(12) United States Patent
Altarac et al.

(10) Patent No.: US 9,855,150 B2
(45) Date of Patent: Jan. 2, 2018

(54) INTERBODY SPACER

(71) Applicants: Moti Altarac, Irvine, CA (US); Joey Reglos, Lake Forest, CA (US); Zafar Khan, Fountain Valley, CA (US); Timothy R. Bumbalough, Fullerton, CA (US)

(72) Inventors: Moti Altarac, Irvine, CA (US); Joey Reglos, Lake Forest, CA (US); Zafar Khan, Fountain Valley, CA (US); Timothy R. Bumbalough, Fullerton, CA (US)

(*) Notice: Subject to any disclaimer, the term of this patent is extended or adjusted under 35 U.S.C. 154(b) by 0 days.

(21) Appl. No.: 14/835,477

(22) Filed: Aug. 25, 2015

(65) Prior Publication Data

US 2017/0056199 A1    Mar. 2, 2017

(51) Int. Cl.
*A61F 2/44* (2006.01)
*A61F 2/30* (2006.01)

(52) U.S. Cl.
CPC .... *A61F 2/4455* (2013.01); *A61F 2002/3093* (2013.01); *A61F 2002/30126* (2013.01); *A61F 2002/30187* (2013.01); *A61F 2002/30622* (2013.01); *A61F 2002/30828* (2013.01); *A61F 2002/30904* (2013.01); *A61F 2002/4475* (2013.01); *A61F 2310/00011* (2013.01)

(58) Field of Classification Search
CPC .......... A61F 2/44; A61F 2/4455; A61F 2/446; A61F 2/4465; A61F 2/447; A61F 2002/4475; A61F 2/442; A61F 2002/30126; A61F 2002/30187; A61F 2002/30622; A61F 2002/30828; A61F 2002/30904; A61F 2002/3093; A61F 2002/30383; A61F 2002/30426; A61F 2002/305; A61F 2002/30517; A61F 2002/30774; A61F 2002/30777; A61F 2002/30843; A61F 2002/30593; A61F 2310/00023; A61F 2310/00011; A61F 2220/0025
USPC ............................................ 623/17.11–17.16
See application file for complete search history.

(56) References Cited

U.S. PATENT DOCUMENTS

| 7,004,944 B2 * | 2/2006 | Gause ................ A61B 17/8047 606/294 |
| 9,364,342 B2 * | 6/2016 | Walkenhorst ........... A61F 2/447 |
| 2013/0345814 A1 * | 12/2013 | Walkenhorst ........... A61F 2/447 623/17.16 |

* cited by examiner

*Primary Examiner* — Pedro Philogene
(74) *Attorney, Agent, or Firm* — Rimas Lukas

(57) ABSTRACT

An interbody spacer for the spine is provided. The interbody spacer includes a polymer cage and a plurality of bone screws configured to anchor the cage between two vertebrae of the spine. The cage includes a screw receiver configured to receive a metallic plate screw for attaching a plate to cover the proximal ends of the bone screws to prevent them from backing out over time with respect to the cage. The screw receiver has deflectable extensions that snap into cage to retain the screw receiver to the cage. The screw receiver also includes a transverse flanges that provide anti-rotation and alignment to the screw receiver relative to the cage and; furthermore, the screw receiver further includes a self-locking feature that increases purchase on the plate screw providing a secured cover plate for anti-backout protection for the bone screws.

20 Claims, 26 Drawing Sheets

INTERBODY SPACER

FIELD OF THE INVENTION

This application relates generally to spinal implants, and in particular, intervertebral spacers and fusion cages.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In a posterior lumbar interbody fusion (PLIF) surgery, spinal fusion is achieved in the lower back by inserting an implant such as a cage and typically graft material to encourage bone ingrowth directly into the disc space between adjacent vertebrae. The surgical approach for PLIF is from the back of the patient, posterior to the spinal column. An anterior lumbar interbody fusion (ALIF) surgical procedure is similar to the PLIF procedure except that in the ALIF procedure, the disc space is fused by approaching the spine through the abdomen from an anterior approach instead of from a posterior approach. Another fusion procedure is called a transforaminal lumbar interbody fusion (TLIF) which involves a posterior and lateral approach to the disc space. To gain access to the disc space, the facet joint may be removed whereby access is gained via the nerve foramen. In an extreme lateral interbody fusion (XLIF), the disc space is accessed from small incisions on the patient's side.

In the typical procedures described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. Once positioned, the interbody spacer is secured to the adjacent vertebrae with one or more bone screws. The implant includes apertures formed at one end for passing one or more bone screws at an upward angle into the first adjacent vertebral body and one or more bone screws at a downward angle into the second adjacent vertebral body.

Over time, the interface between the screws and the bone may present some problems of stability. Due to the anatomical structure of the spine and the extreme anatomical forces that are brought to bear on the skeleton and transmitted to the vertebral bodies, the screws securing the interbody spacer to the spine may vibrate or toggle out of position. Also, the degeneration of vertebral bone quality may result in the screws loosening or becoming dislodged. As a result, bone screws securing the plate to the spine may move or back out of the vertebral body and implant. Loosened screws may result instability of the joint and lead to increased pain for the patient.

Therefore, there is a need to provide a new and improved interbody spacer that resists fasteners, such as bone screws, from backing out and also from being loosened with respect to the implant before migrating out. Furthermore, there is a need for the implant to withstand anatomical forces and be easily implanted. Also, the screw retaining mechanism must be easily activated by the surgeon. This invention, as described in the detailed description, sets forth an improved interbody spacer that meets these needs.

SUMMARY OF THE INVENTION

According to one aspect of the invention, an interbody spacer for the spine is provided. The interbody spacer includes a cage having a top surface and a bottom surface interconnected by a sidewall. The cage includes a central opening extending between the top surface and the bottom surface that defines an inner surface. The cage includes a plurality of bone screw apertures opening in the sidewall. The cage also includes a screw receiver aperture. The screw receiver aperture is sized and configured to receive a screw receiver. The interbody spacer further includes a screw receiver connected to the cage and located inside the screw receiver aperture. The screw receiver has a longitudinal axis and a threaded lumen extending between a proximal end and a distal end along the longitudinal axis of the screw receiver. The interbody spacer further includes a plate screw having a proximal end and a threaded shank. The plate screw is sized and configured to be threadingly and removably received inside the threaded lumen of the screw receiver. The interbody spacer further includes a cover plate having an inner surface and an outer surface. The cover plate has a plate screw aperture extending between the inner surface and the outer surface. The cover plate is removably connected to the sidewall of the cage with a plate screw inserted into the plate screw aperture and threaded into the lumen of the screw receiver. The interbody spacer further includes a plurality of bone screws disposed inside the plurality of bone screw apertures. Each bone screw has a head at a proximal end and a threaded shank extending toward a distal end for anchoring into bone. The plurality of bone screws is configured to anchor the interbody spacer between two bony components of the spine. The cover plate is disposed over the head of at least one of the plurality of bone screws when attached to the cage to retain the at least one bone screw and prevent the at least one bone screw from backing out.

According to another aspect of the invention, an interbody spacer for the spine is provided. The interbody spacer includes a cage having a top surface and a bottom surface interconnected by a sidewall. The cage has a central opening extending between the top surface and the bottom surface and defining an inner surface. The cage includes at least one bone screw aperture opening in the sidewall. The cage includes a screw receiver aperture. The screw receiver aperture is sized and configured to receive a screw receiver. The interbody spacer further includes a screw receiver connected to the cage and located inside the screw receiver aperture. The screw receiver has a threaded lumen extending between a proximal end and a distal end. The screw receiver has at least one slit extend from the distal end toward the proximal end that divides the distal end of the screw receiver into at least one deflectable extension. The interbody spacer further includes a plate screw having a proximal end and a threaded shank. The plate screw is sized and configured to be threadingly and removably received inside the threaded lumen of the screw receiver. The interbody spacer further includes a cover plate having an inner surface and an outer surface. The cover plate includes a plate screw aperture extending between the inner surface and the outer surface. The cover plate is removably connected to the sidewall of the cage with a plate screw inserted into the plate screw aperture and threaded into the lumen of the screw receiver. The interbody spacer further includes at least one bone screw disposed inside the at least one bone screw aperture. Each bone screw has a head at a proximal end and a threaded shank extending toward a distal end for anchoring into bone. The at least one bone screw is configured relative to the cage to anchor the interbody spacer between two bony components of the spine. The cover plate is disposed over the head of the at least one of the bone screws when attached to the cage to retain the at least one bone screw and prevent the at least one bone screw from backing out. In one variation, the screw receiver aperture extends between the sidewall and inner surface and the screw receiver has an outwardly extending detent. The detent resides against the inner surface of the cage or, in another variation, within an inner ridge when connected to the cage. The detent is configured to prevent the screw receiver from moving proximally within the cage. When the screw receiver is inserted into the screw receiver aperture, the extensions deflect inwardly and snap outwardly when the detent exits screw receiver aperture at the inner surface of the cage or in another variation, snap outwardly into the inner ridge.

According to another aspect of the invention, an interbody spacer for the spine is provided. The interbody spacer includes a cage having a top surface and a bottom surface interconnected by a sidewall. The cage includes a central opening extending between the top surface and the bottom surface and defining an inner surface. The cage includes at least one bone screw aperture opening in the sidewall. The cage includes a screw receiver aperture. The screw receiver aperture is sized and configured to receive a screw receiver. The interbody spacer further includes a screw receiver connected to the cage and located inside the screw receiver aperture. The screw receiver has a threaded lumen along a longitudinal axis. The screw receiver includes one or more wings extending transverse to the longitudinal axis of the screw receiver. The interbody spacer includes a plate screw having a proximal end and a threaded shank. The plate screw is sized and configured for being threadingly and removably received inside the threaded lumen of the screw receiver. The interbody spacer includes a cover plate having an inner surface and an outer surface and a plate screw aperture extending between the inner surface and the outer surface. The cover plate is removably connected to the sidewall of the cage with a plate screw inserted into the plate screw aperture and threaded into the lumen of the screw receiver. The interbody spacer further includes at least one bone screw disposed inside the at least one of the bone screw apertures. Each bone screw has a head at a proximal end and a threaded shank extending toward a distal end for anchoring into bone. At least one bone screw is configured to anchor the interbody spacer between two bony components of the spine. The cover plate is disposed over the head of at least one of the bone screws when attached to the cage to retain the bone screw and prevent the bone screw from backing out.

According to another aspect of the invention, an interbody spacer for the spine is provided. The interbody spacer includes a cage having a top surface and a bottom surface interconnected by a sidewall. The cage includes a central opening extending between the top surface and the bottom surface and defining an inner surface. The cage includes at least one bone screw apertures opening in the sidewall. The cage also includes a screw receiver aperture. The screw receiver aperture is sized and configured to receive a screw receiver. The screw receiver aperture intersects with a bone screw aperture to form a scallop-shaped intersection. The interbody spacer also includes a screw receiver connected to the cage and located inside the screw receiver aperture. The screw receiver has a longitudinal axis and a threaded lumen extending between a proximal end and a distal end along the longitudinal axis of the screw receiver. The screw receiver includes one or more wings extending transverse to the longitudinal axis. The screw receiver has a scallop opening at the proximal end and extending longitudinally toward the distal end. The scallop substantially corresponds in size and shape with the scallop-shaped intersection. The interbody spacer further includes a plate screw having a proximal end and a threaded shank. The plate screw is sized and configured for being threadingly and removably received inside the threaded lumen of the screw receiver. The interbody spacer also includes a cover plate having an inner surface and an outer surface and a plate screw aperture extending between the inner surface and the outer surface. The cover plate is removably connected to the sidewall of the cage with a plate screw inserted into the plate screw aperture and threaded into the lumen of the screw receiver. The interbody spacer further includes at least one bone screw disposed inside the at least one bone screw aperture. Each bone screw has a head at a proximal end and a threaded shank extending toward a distal end for anchoring into bone. At least one bone screw is configured to anchor the interbody spacer between two bony components of the spine. The cover plate is disposed over the head of at least one of the bone screws when attached to the cage to retain the bone screw and prevent the bone screw from backing out. The sidewall of the cage includes a screw receiver recess sized and configured to recess the one or more wings to prevent rotation of the screw receiver relative to the cage and to align the scallop of screw receiver with the scallop-shaped intersection. The screw receiver has at least one slit extending from the distal end toward the proximal end that divides the distal end of the screw receiver into at least one deflectable extension.

DETAILED DESCRIPTION OF THE INVENTION

Figure 1:
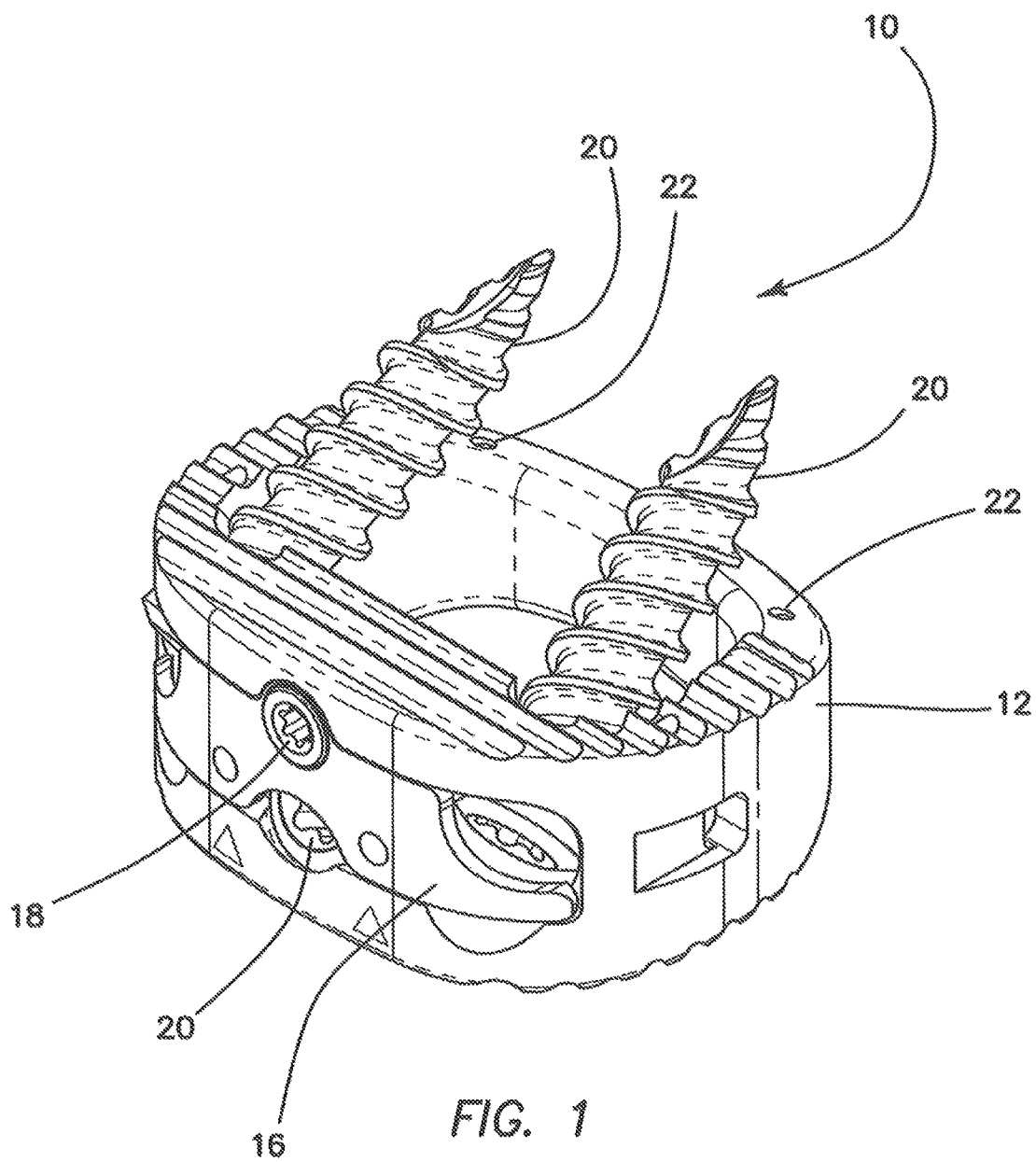
FIG. 1 is a top perspective view of an interbody spacer according to the present invention.
Figure 2:
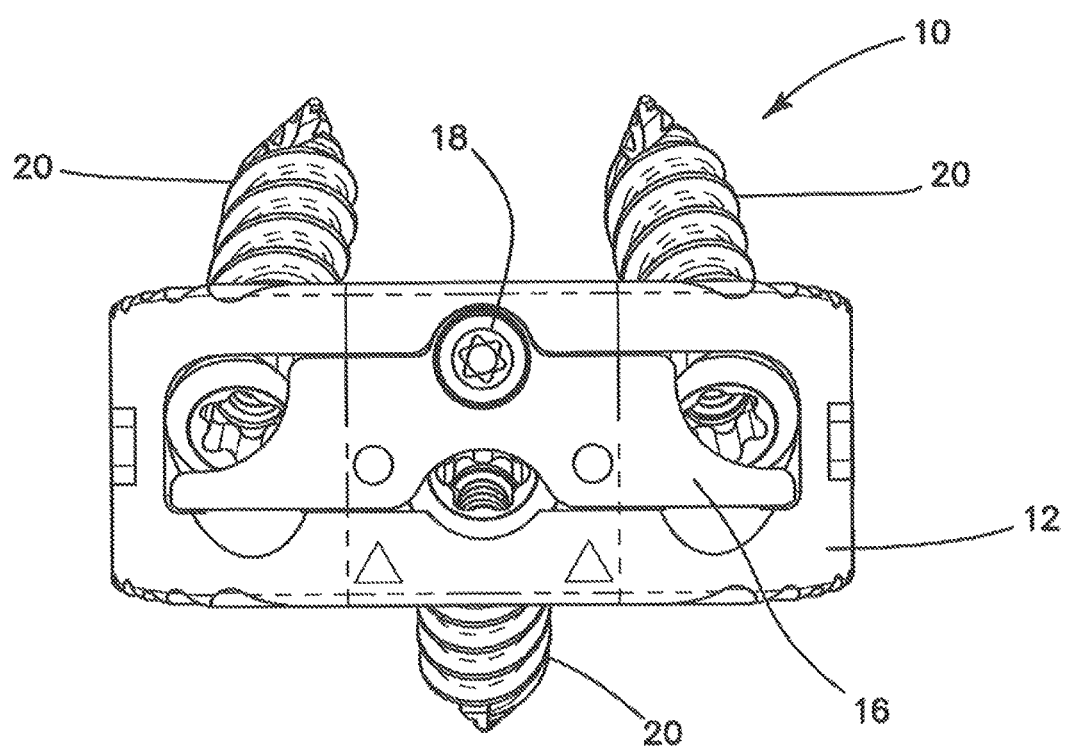
FIG. 2 is a front elevational view of an interbody spacer according to the present invention.
Figure 3:
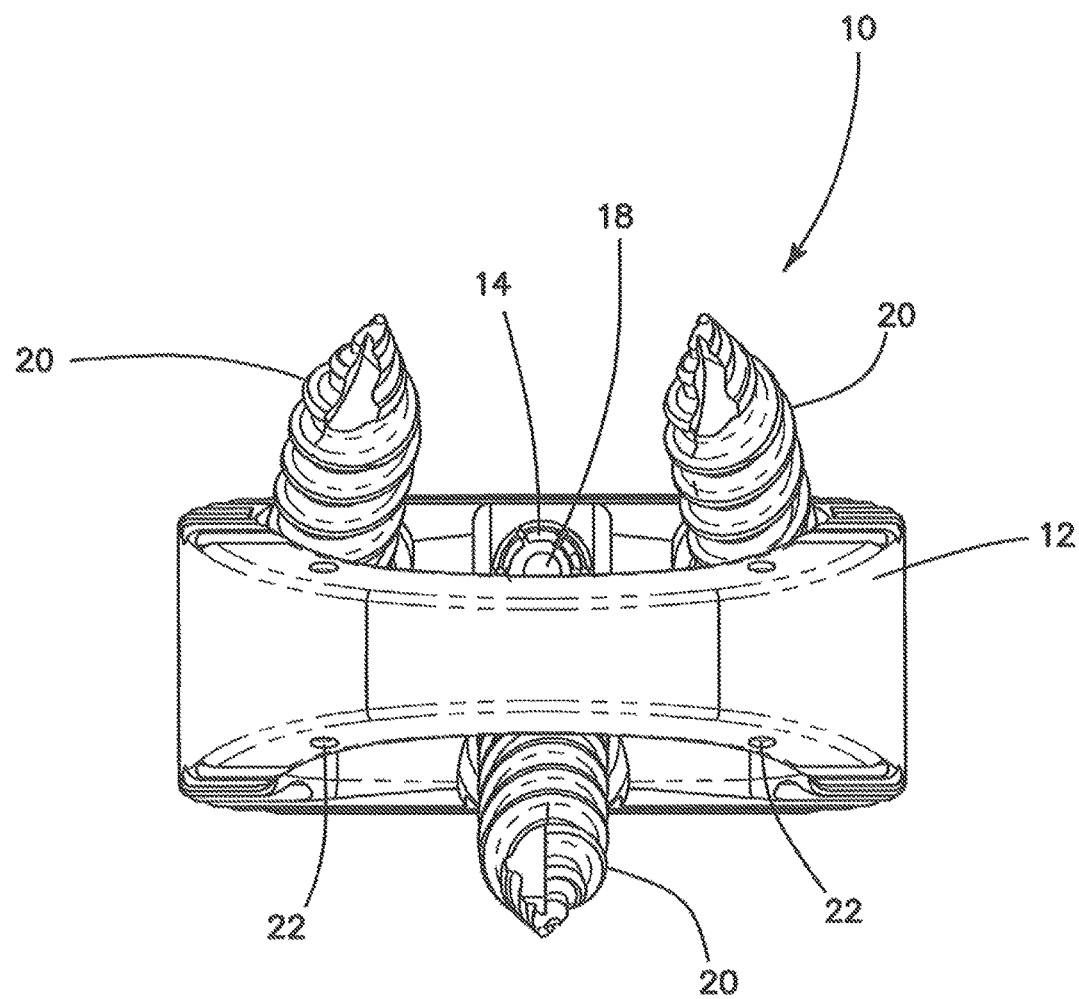
FIG. 3 is a rear elevational view of an interbody spacer according to the present invention.
Figure 4:
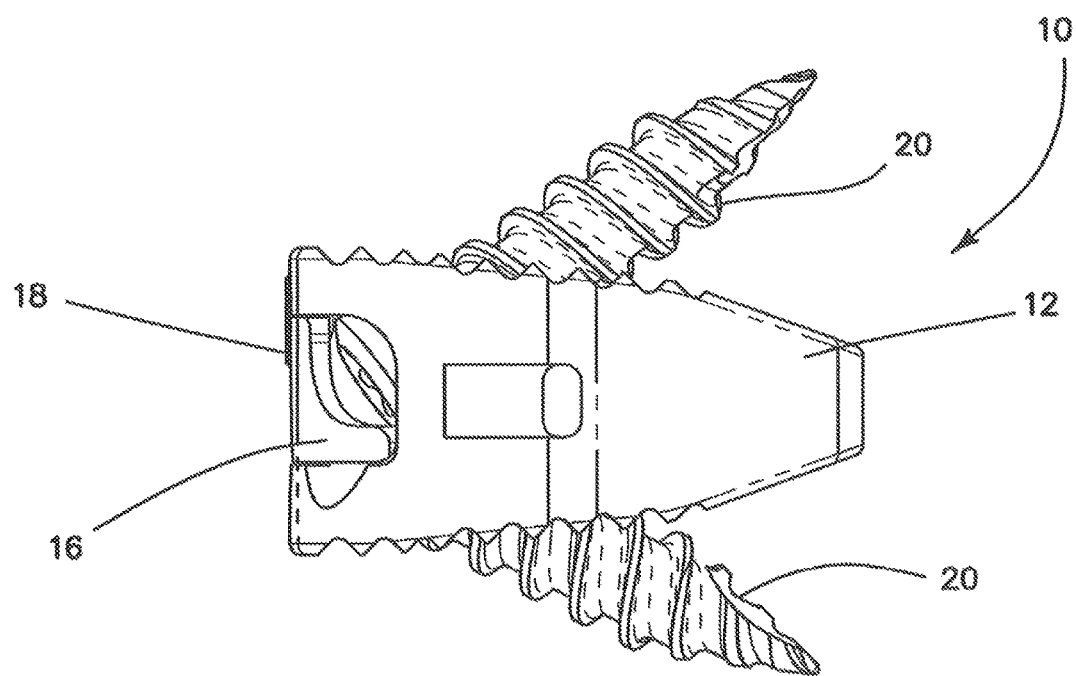
FIG. 4 is a side elevational view of an interbody spacer according to the present invention.
Figure 5:
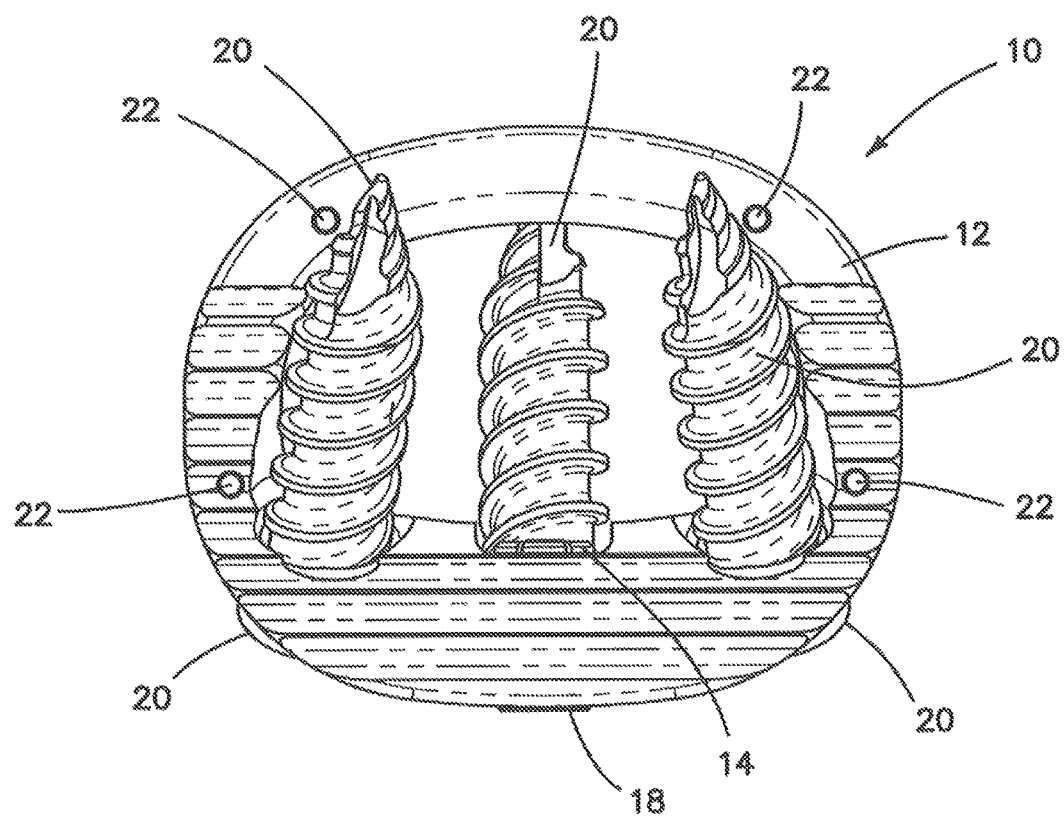
FIG. 5 is a top planar view of an interbody spacer according to the present invention.
Figure 6:
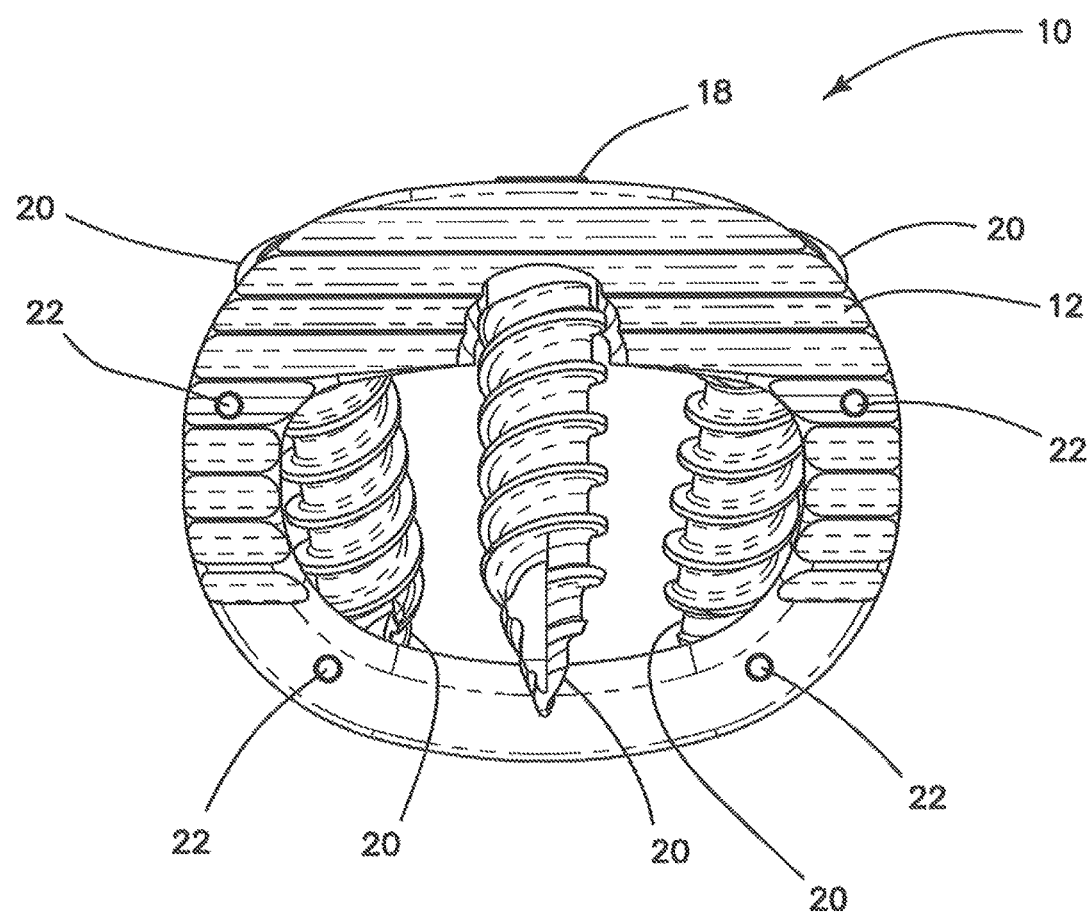
FIG. 6 is a bottom planar view of an interbody spacer according to the present invention.
Figure 7:
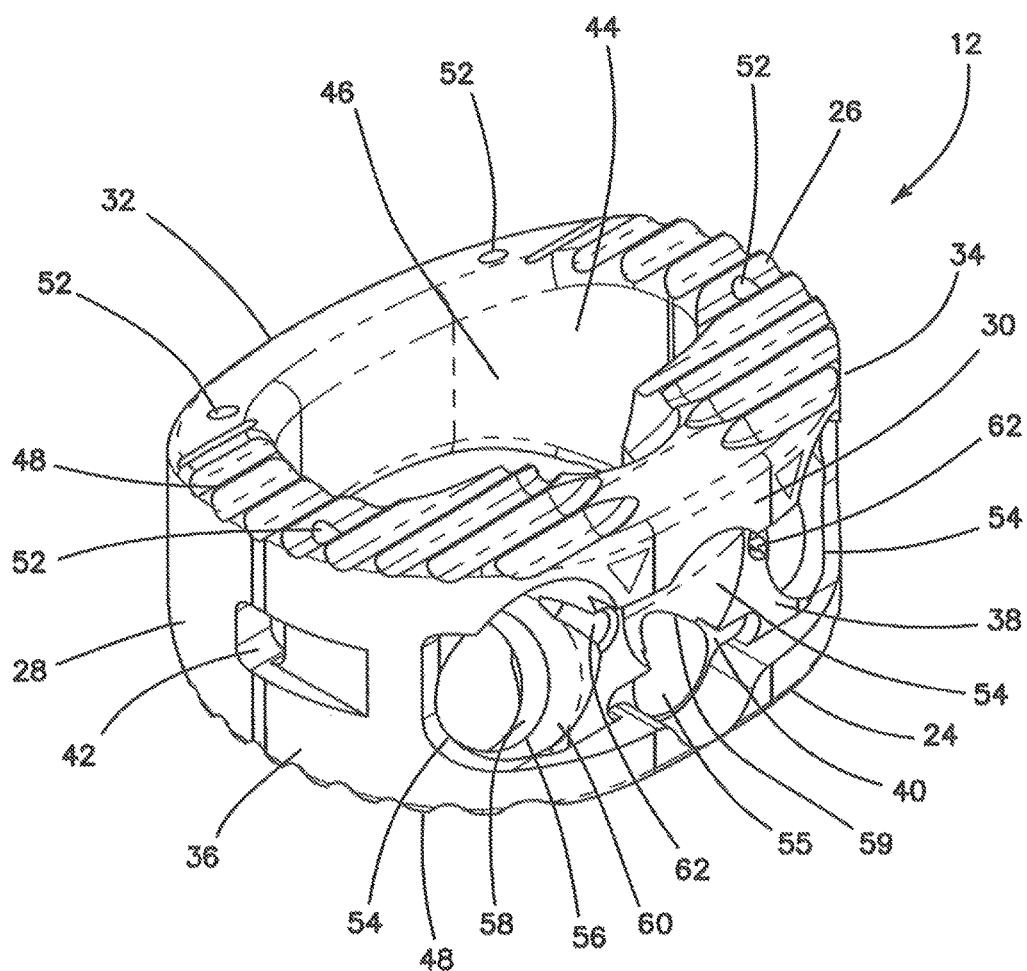
FIG. 7 is a bottom perspective view of a cage according to the present invention.
Figure 8:
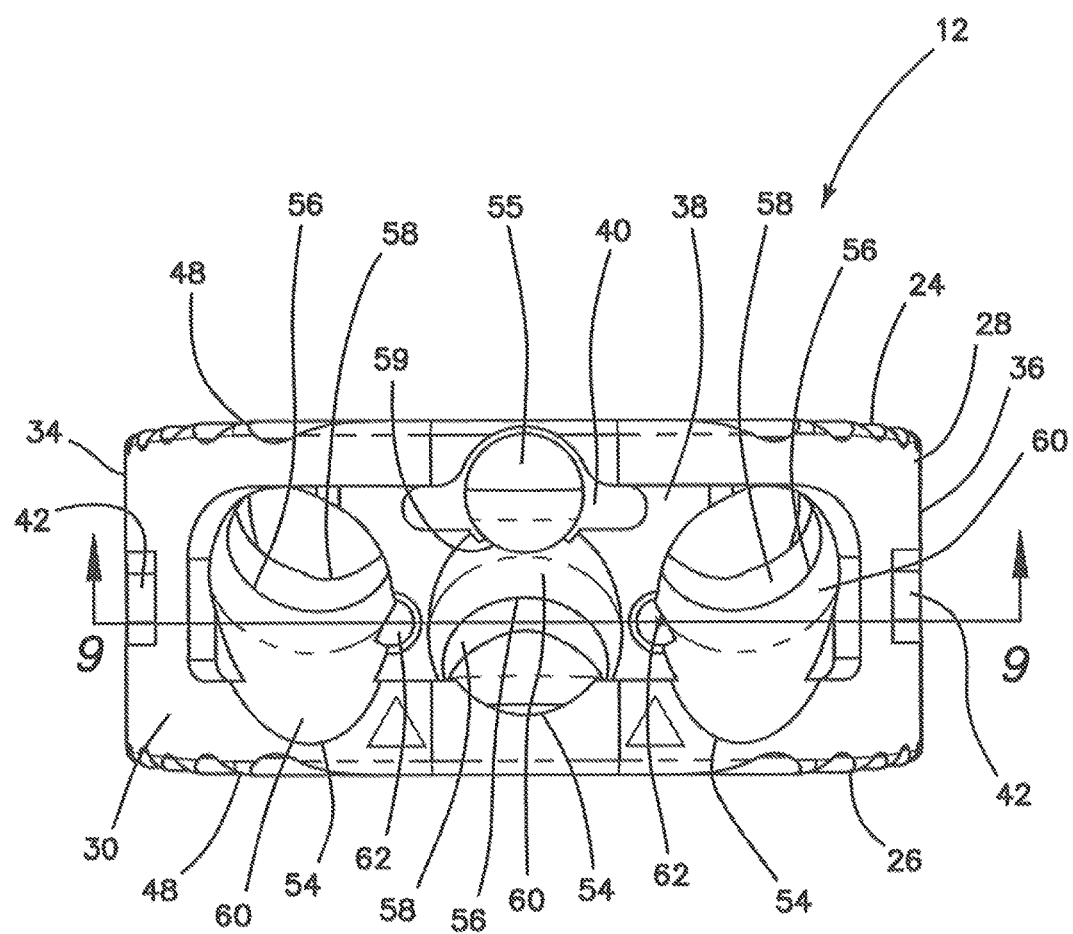
FIG. 8 is a front elevational view of a cage according to the present invention.
Figure 9:
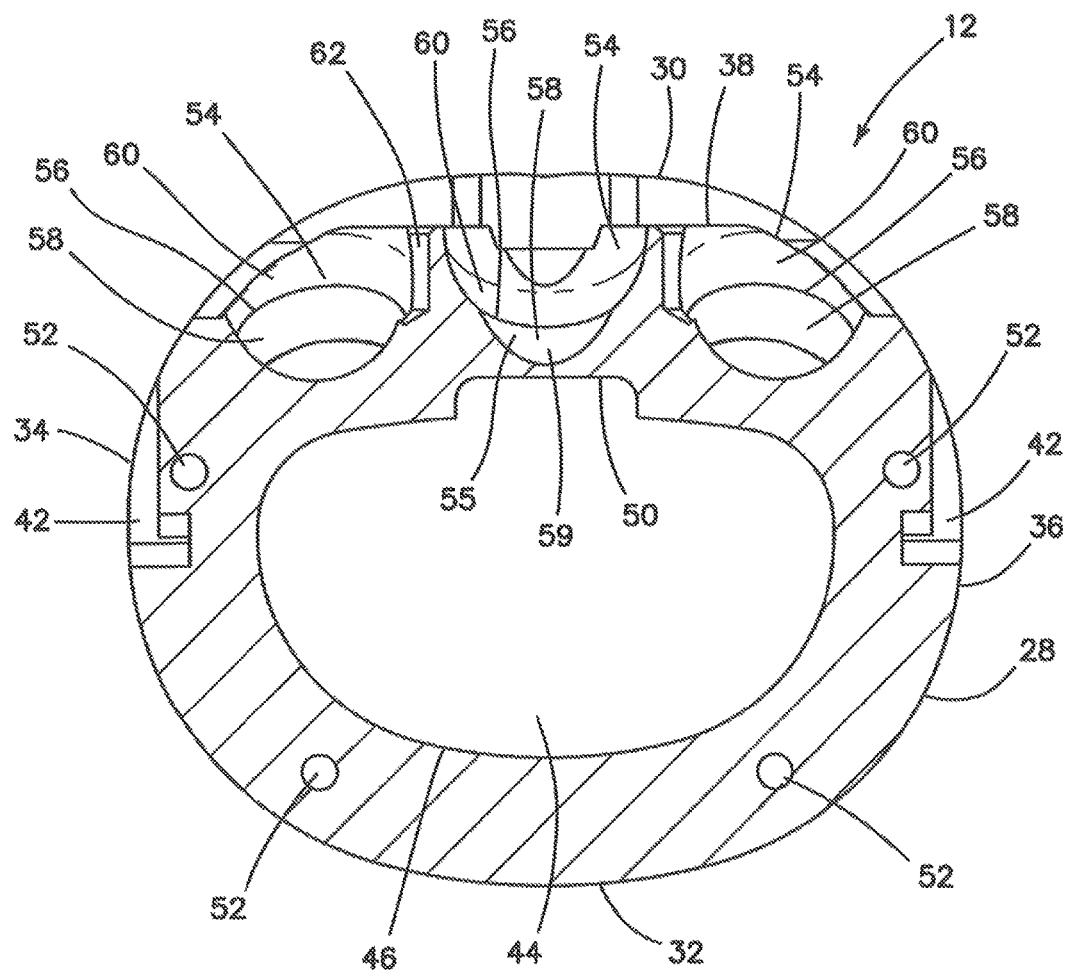
FIG. 9 is a cross-sectional view taken along line 9-9 of FIG. 8 of a cage according to the present invention.
Figure 10:
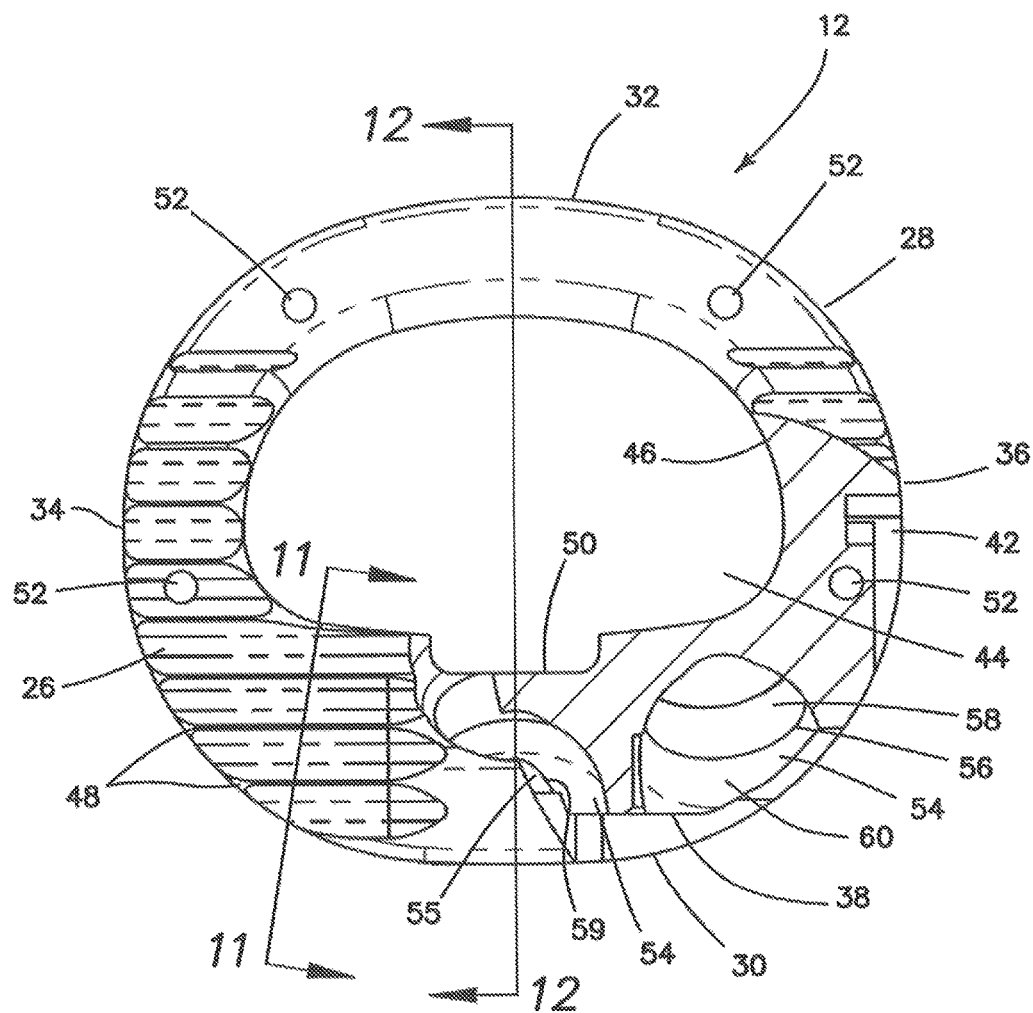
FIG. 10 is a bottom sectional view of a cage according to the present invention.
Figure 11:
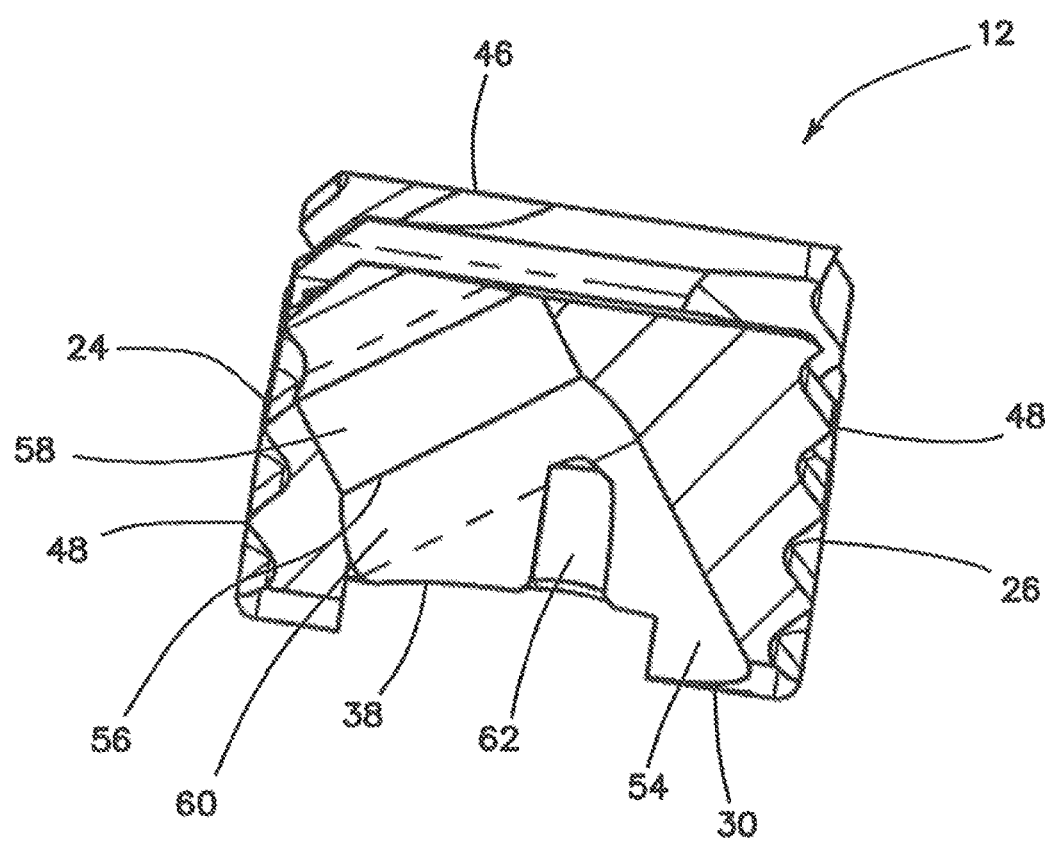
FIG. 11 is a cross-sectional view taken along line 11-11 of FIG. 10 of a cage according to the present invention.

FIGS. 1-6 depict an interbody spacer 10 according to one variation of the invention that may be used to stabilize or fuse vertebral bodies in the lumbar or other region of the spine. The interbody spacer 10 comprises a cage 12, a screw receiver 14, a cover plate 16, a plate screw 18, and bone screws 20. The screw receiver 14 is connected to the cage 12 to receive a plate screw 18 to secure the cover plate 16 to the cage 12 in order to retain the bone screws 20 disposed in the cage 12. The bone screws 20 are configured relative to the cage to anchor the interbody spacer 10 between two bony components of the spine. Optional radiographic markers 22 are embedding within the cage 12.

Figure 12:
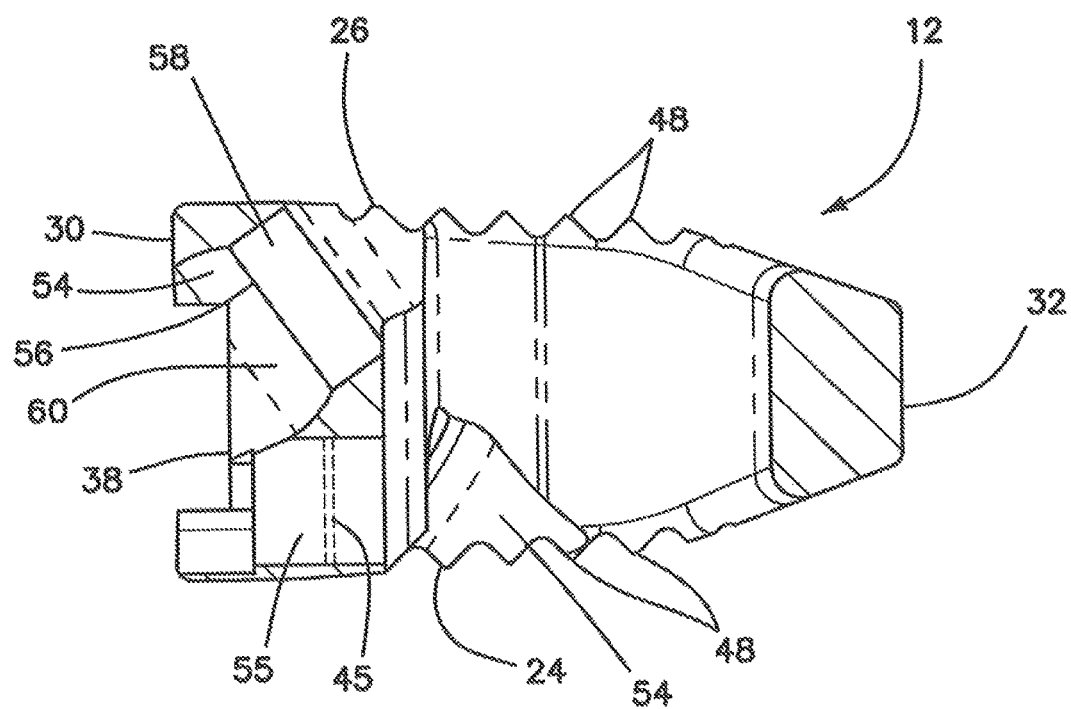
FIG. 12 is a cross-sectional view taken along line 12-12 of FIG. 10 of a cage according to the present invention.
Figure 13:
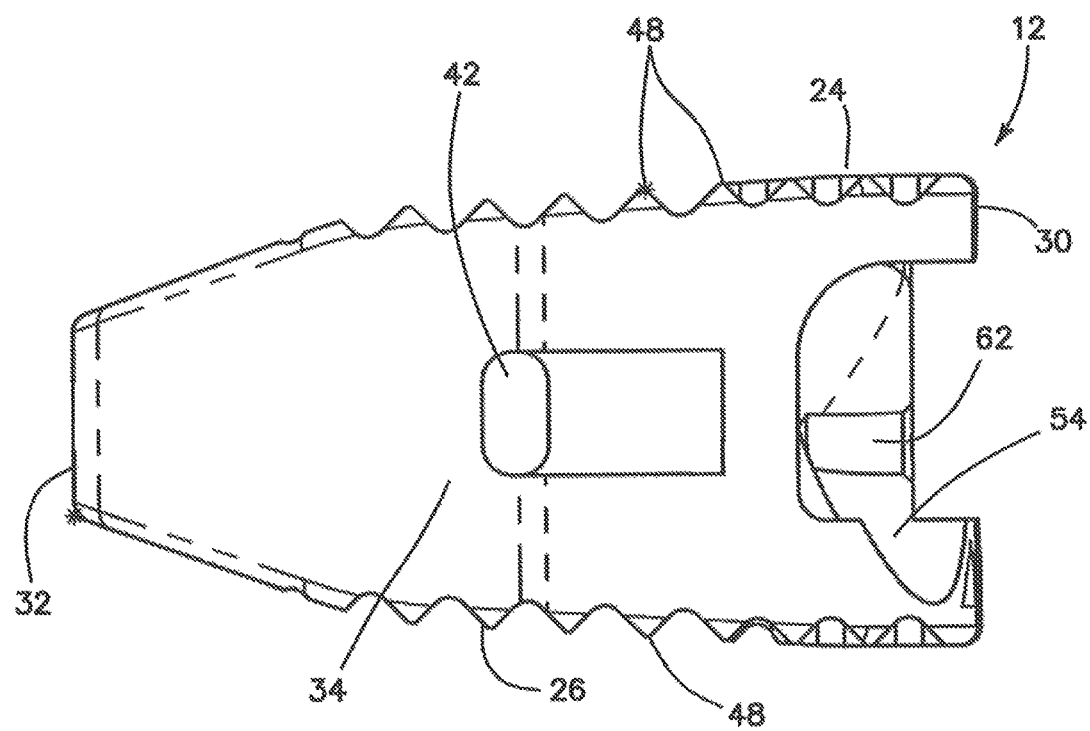
FIG. 13 is a side elevational view of a cage according to the present invention.
Figure 14:
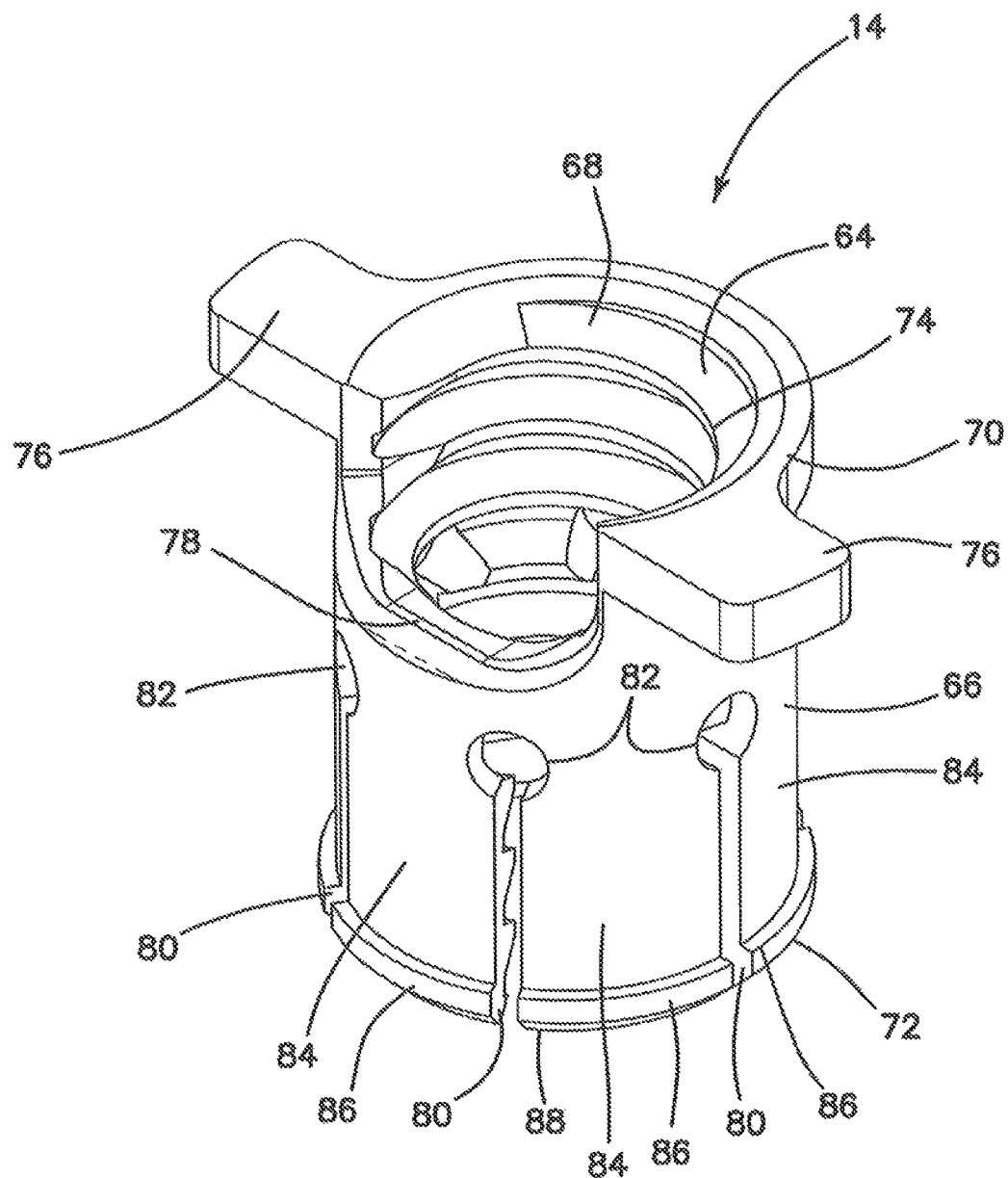
FIG. 14 is a top perspective view of a screw receiver according to the present invention.
Figure 15:
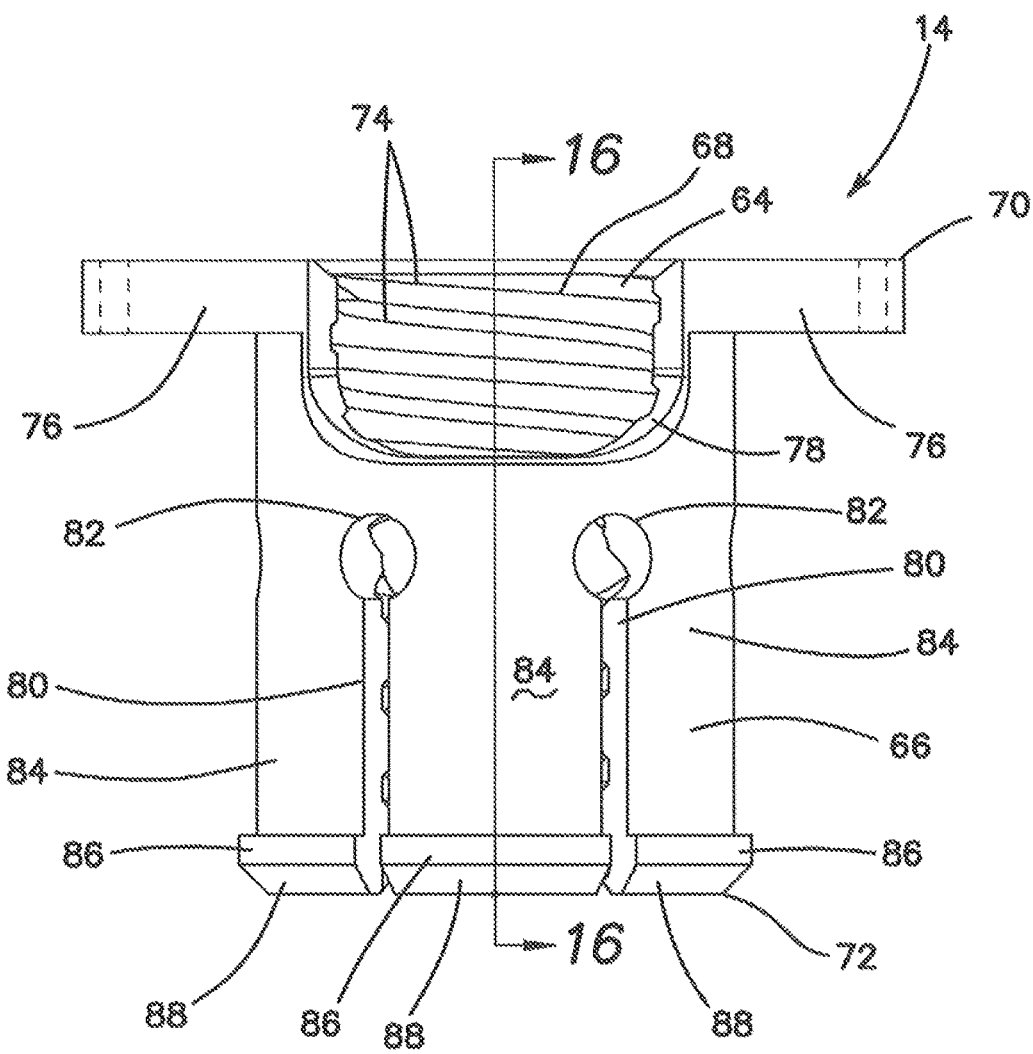
FIG. 15 is a side elevational view of a screw receiver according to the present invention.
Figure 16:
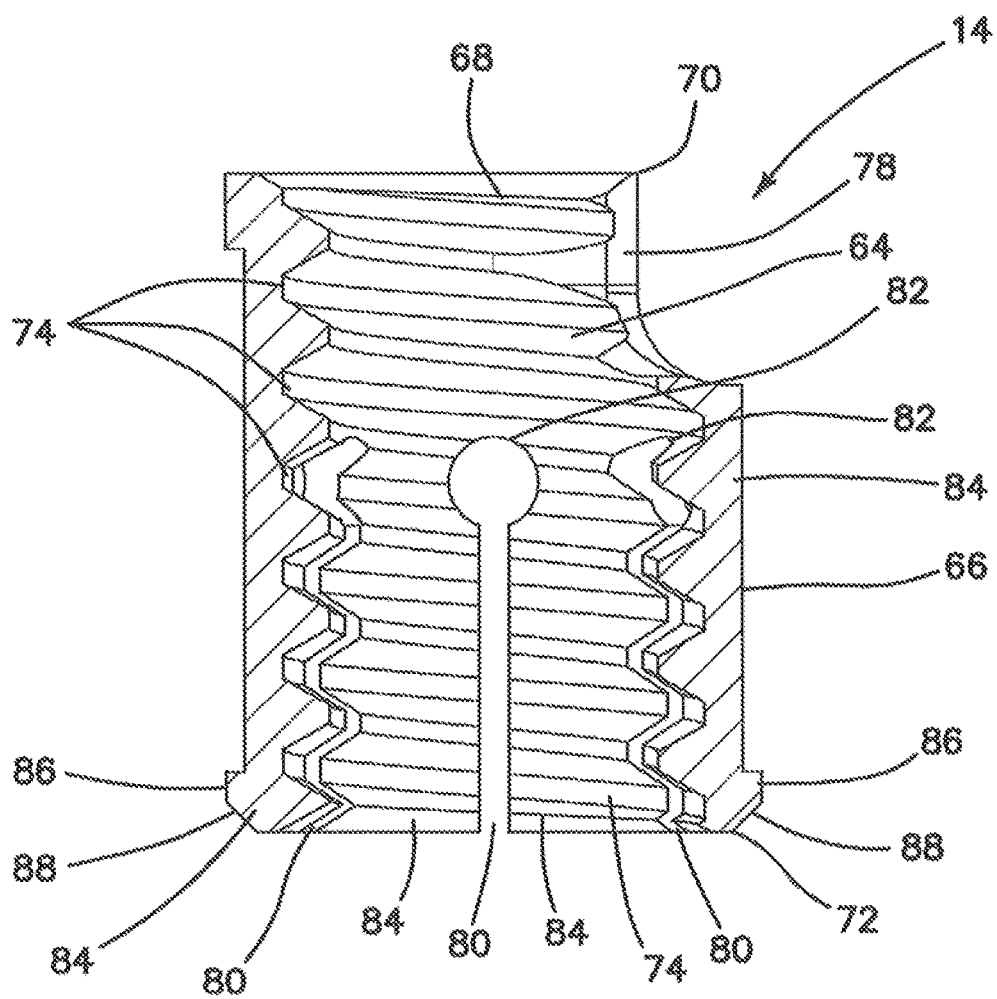
FIG. 16 is a cross-sectional view taken along line 16-16 of FIG. 15 of a screw receiver according to the present invention.
Figure 17:
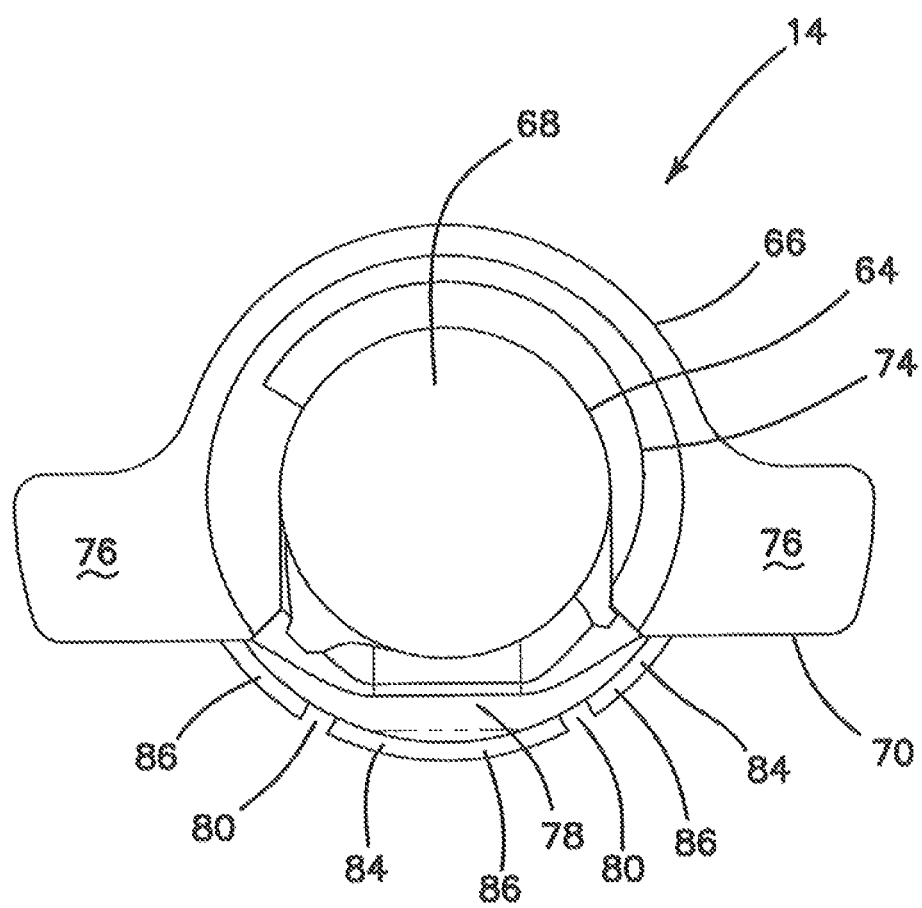
FIG. 17 is a top planar view of a screw receiver according to the present invention.
Figure 18:
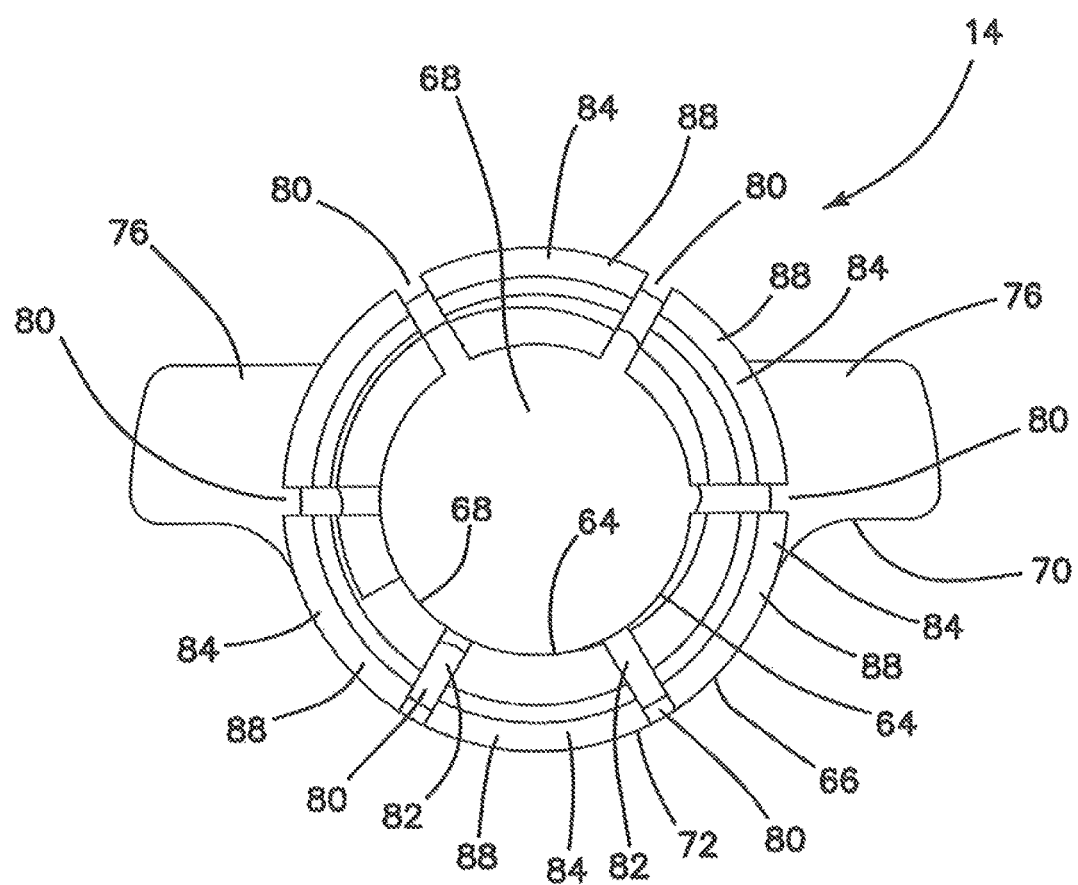
FIG. 18 is a bottom planar view of a screw receiver according to the present invention.

Turning now to the FIGS. 7-13, the cage 12 will now be described in greater detail. The cage 12 includes a top surface 24 and a bottom surface 26 interconnected by at least one sidewall 28 extending between the top surface 24 and the bottom surface 26 defining a cage height. The cage 12 has a shape that mimics a spinal disc. The sidewall 28 has an anterior surface 30 and a posterior surface 32 interconnected by two side surfaces 34, 36. The anterior surface 30 has a larger cage height relative to the posterior surface 32 imparting the cage 12 with a wedge-like configuration having a taper from the anterior surface 30 to the posterior surface 32 as can be seen in FIG. 13. This taper is designed to accommodate the natural anatomic relationship between adjacent vertebral bones and maintain the normal lordotic curvature of the spine. The cage 12 has a lordotic angle that is between approximately 5 degrees and 15 degrees. The cage 12 has a cage height of approximately 10-20 mm such as approximately 12 mm, 14 mm, 16 mm and 18 mm. The anterior and posterior surfaces 30, 32 are longer than the side surfaces 34, 36 when measured along a lateral dimension giving the cage 12 an elongate shape when viewed along the longitudinal axis. The lateral dimension of the cage 12 as measured between side surfaces 34, 36 is approximately 25 mm-40 mm and the anterior-to-posterior dimension is approximately 20 mm-30 mm. The intersections of the surfaces 30, 32, 34 and 36 are smooth and rounded giving the cage 12 an overall oval or oblong shape.

The anterior surface 30 of the cage 12 includes a cover plate recess 38. The cover plate recess 38 is sized and configured to conform and to receive the cover plate 16. When the cover plate 16 is attached to the cage 12, the cover plate 16 is recessed such that the cover plate 16 does not significantly protrude or extend outwardly from the anterior surface 30. In one variation, the depth of the cover plate recess 38 substantially equals the thickness of the cover plate 16 such that the cover plate 16 is flush with the anterior surface 30 when attached to the cage 12. Within the cover plate recess 38, a screw-receiver recess 40 is formed. The screw-receiver recess 40 is sized and configured to receive at least a portion of the screw receiver 14 such that the screw receiver 14 does not protrude or extend into the cover plate recess 38 as doing so would prevent the cover plate 16 from seating neatly within the cover plate recess 38.

The side surfaces 34, 36 of the cage 12 each include instrument notches 42 which serve as tool receiving recesses that are sized and configured to receive oppositely disposed distal prongs of an insertion instrument used for delivering, implanting and removing the interbody spacer 10. The instrument notches 42 are formed laterally oppositely from each other near the lateral axis of the cage 12. The instrument notches 42 may include a ramped surface such that the prongs of an insertion instrument do not unduly extend laterally outwardly from the side surfaces 34, 36.

The top surface 24 or superior surface of the cage 12 is configured for engaging a lower endplate of a first vertebral bone and the bottom surface 26 or inferior surface of the cage 12 is configured for engaging an upper endplate of an adjacent second vertebral bone of the spine. The top and bottom surfaces 24, 26 are spaced apart with the sidewall 28 extending therebetween. The top and bottom surfaces 24, 26 define a longitudinal axis extending substantially normal to the top and bottom surfaces 24, 26. It is understood that the longitudinal axis is not precisely normal to the top and bottom surfaces 24, 26 due to the narrowing height and lordotic angle of the cage 12 from the anterior surface 30 to the posterior surface 32. The longitudinal axis of the cage 12 is approximately parallel to or substantially coaxial with the longitudinal direction of the spine when the interbody spacer 10 is implanted. Extending between the top surface 24 and the bottom surface 26 is a central cage opening 44 having an opening at the top surface 24 and extending to an opening at the bottom surface 26 and, thereby, defining an inner surface 46 and central lumen of the cage 12. The central cage opening 44 reduces the weight of the cage 12 and permits bone ingrowth to take place into and through the cage 12. A family of bone graft materials, such as autograft, bone morphogenic protein (BMP), bone marrow aspirate, concentrate, stem cells and the like, may be placed inside the central cage opening 44 to promote bone growth into the cage 12. A plurality of ridges 48 are formed on the top surface 24 and the bottom surface 26. The ridges 48 have pointed peaks to engage and increase the purchase on the endplates of adjacent vertebra. The ridges 48 may further be angled with respect to the top and bottom surfaces 24, 26 such that the ridges 48 help to hold and prevent migration of the cage 12 relative to the adjacent vertebrae when implanted within the intervertebral space. The inner surface 46 of the cage 12 includes an inner recess 50 substantially oppositely disposed from the screw receiver recess 40. The inner recess 50 is configured to receive at least part of the distal end of the screw receiver 14. The top surface 24 and/or the bottom surface 26 of the cage 12 may include one or more radiographic pin holes 52 for receiving radiographic markers 22.

The cage 12 further includes one or more bone screw apertures 54 formed in the sidewall 28 and extending to one or more of the top surface 24 and the bottom surface 26. In the variation shown in FIGS. 7-13, two bone screw apertures 54 are formed in the anterior surface 30 in the location of the cover plate recess 40 and the bone screw apertures 54 extend transversely across the sidewall 28 and open into the inner surface 46 of the cage 12. One or more bone screw apertures 54 are angled toward the top surface 24 such that bone screws 20 inserted therein are directed into the lower endplate of the adjacent upper vertebra. Two bone screw apertures 54 are shown angled upwardly toward the upper vertebral body. One or more bone screw apertures 54 are angled toward the bottom surface 26 such that bone screws 20 inserted therein are directed into the upper endplate of the adjacent lower vertebra. One bone screw aperture 54 is shown angled downwardly toward the lower vertebral body. Each bone screw aperture 54 includes an interior ledge 56 for contact with the head of the bone screw 20. The interior ledge 56 divides the bone screw aperture 54 into a bone screw shaft receiving portion 58 and a bone screw head receiving portion 60. The inner diameter of the head receiving portion 60 is larger than the inner diameter of the shaft receiving portion 58 to accommodate the relatively larger head of the bone screw 20 and to permit it to angulate substantially polyaxially. The angulation of the bone screw aperture 54 results in a fluted entry best seen in FIG. 13. All of the bone screw apertures 54 are formed in the location of the cover plate recess 38 such that when the cover plate 16 is installed, it covers all of the bone screws 20 inserted therein to prevent them from backing out of the cage 12. The bone screw aperture 54 that is angled downwardly is formed between the two bone screw apertures 54 that are angled upwardly and substantially along the midline of the cage 12.

The cage 12 further includes a screw receiver aperture 55 formed in the screw receiver recess 40 and extending from the anterior surface 30 through the sidewall 28 and opening into the inner surface 46 of the cage 12. The screw receiver aperture 55 is sized and configured to receive the screw receiver 14 such that the screw receiver 14 is recessed with respect to the cover plate recess 38. The screw receiver aperture 55 intersects with one of the bone screw apertures 54 forming an intersecting scallop 59. In particular, the screw receiver aperture 55 intersects with the bone screw aperture 54 that is angled downwardly into the upper endplate of a lower adjacent vertebra. The screw receiver aperture 55 is located approximately along the midline and also one of the bone screw apertures 54 is also located along the midline and due to their close proximity the intersection creates a scallop-shaped intersection or notch into the screw receiver aperture 55. In particular, the head receiving portion 60 of the intersecting bone screw aperture 54 has a larger diameter to permit polyaxial angulation of the bone screw relative to the cage 12. In order to not obstruct insertion and angulation of the bone screw and due to the close proximity of the bone screw aperture 54 and the screw receiver aperture 55, a scallop 59 is formed.

The cage 12 further includes two guide apertures 62. The guide apertures 62 are formed in the location of the cover plate recess 38 on either side of one of the bone screw apertures 54. In one variation, the guide apertures 62 are formed on either side of the bone screw aperture 54 that is angled downwardly. The guide apertures 62 are configured to connect with an instrument configured to align and attach the cover plate 16 and plate screw 18 to the cage 12 upon its implantation which will be discussed below in greater detail. In brief, the instrument that is used to attach the cover plate 16 includes two pins that are passed through corresponding holes in the cover plate 16. With the cover plate 16 attached to the instrument, the cover plate 16 is delivered on the instrument to the anterior surface 30 and aligned with the cage 12 by passing the distal end ends of the pins into the guide apertures 62 bringing the cover plate 16 and plate screw 18 into proper alignment and attachment to the cage 12.

Turning now to FIGS. 14-18, the screw receiver 14 will now be described in greater detail. The screw receiver 14 serves as an interface for receiving a metal screw. The screw receiver 14 receives a metallic plate screw 18 that is used to attach a metal cover plate 16 to the cage 12 that is not made of metal. The cover plate 16 helps retain bone screws 20 used in conjunction with the cage 12 and helps prevent the bone screws 20 from backing out with respect to the cage 12. Polyether ether ketone (PEEK) is a thermoplastic polymer that has been widely accepted for use in the manufacture of medical implants. PEEK has excellent mechanical, chemical resistance and biocompatible properties and has been finding increased use in spinal fusion devices as it mimics the stiffness of real bone. While many medical implants are made entirely of PEEK, many implants have both PEEK components and non-PEEK components such as stainless steel and titantium. The screw receiver 14 is made of metal such as surgical stainless steel and titanium for receiving a metallic plate screw 18. The screw receiver 14 is a cylindrical plug having an inner surface 64 and an outer surface 66. In another variation, the screw receiver 14 is not cylindrical but can have any symmetrical or asymmetrical shape. A screw receiver 14 with an asymmetrical outer surface is configured to fit within a complementary-shaped asymmetrical screw receiver aperture 55 in the cage 12. An asymmetrical screw receiver 14 advantageously aligns the screw receiver 14 with respect to the cage 12. The screw receiver 14 includes a lumen 68 defined by the inner surface 64 and having an opening at the proximal end 70 and interconnected with an opening at the distal end 72. The inner surface 64 of the lumen 68 has threads 74 for engaging with the complementary threads on the plate screw 18. The proximal end 70 of the screw receiver 14 includes one or more projection or wing 76 extending laterally outwardly from the outer surface 66. In FIGS. 14-18, the screw receiver 14 has a pair of oppositely disposed wings 76 at the proximal end 70. The wings 76 have a shape and thickness that substantially corresponds to the shape and thickness of the screw receiver recess 40 formed in the cage 12. The screw receiver 14 has a scallop 78 extending from the proximal end 70 toward the distal end 72. The scallop 78 is an opening or notch into the sidewall of the screw receiver 14 that is interconnected with the lumen opening at the proximal end 70. The scallop 78 corresponds substantially to the shape and size of the scallop 59 formed in the cage 12 at the intersection of the bone screw aperture 54 and one or more of the screw receiver recess 40 and screw receiver aperture 55. The screw receiver 14 further includes a plurality of slits 80 circumferentially formed about the distal end 72. Each slit 80 extends from the distal end 72 toward a radiused curved proximal end 82. The slits 80 form a plurality of fingers or finger-like, deflectable extensions 84 at the distal end 72 of the screw receiver 14. Although a plurality of slits 80 are shown, only one slit 80 is required to divide the distal end into at least one deflectable extension 84. The perimeter at the distal end 70 of screw receiver 14 includes at least one detent 86 extending outwardly from the outer surface 66 of the screw receiver 14. Each finger-like extension 84 is configured to be capable being deflected inwardly toward the longitudinal axis of the screw receiver 14 and then spring back toward its normal state from the flexed position. The distal end 72 may include a beveled or ramped surface 88 to ease installation of the screw receiver 14 into the cage 12. As the screw receiver 14 is inserted the distal end will lead the insertion and the ramped surface 88 will facilitate deflection of the extensions toward the longitudinal axis. As the screw receiver 14 passes through the screw receiver aperture 55, the detent 86 of each extension 84 will exit at the inner surface of the cage 12 and spring outwardly toward the undeflected position, hooking the distal end at the inner surface of the cage 12 and, thereby, preventing the screw receiver 14 from being removed in the proximal direction.

In one variation, the lumen 68 of the screw receiver 14 is tapered such that the inner diameter along the longitudinal axis decreases with progressively distal cross-sections. The inside taper includes the threads 74 and the taper is configured such that when a plate screw 18 is inserted into the screw receiver, the taper will force the distal fingerlike extensions 84 laterally outwardly as a plate screw 18 is threaded further distally into the lumen 68. The slits 80 permit the flexure of the extensions 84 in the lateral direction to the longitudinal axis of the screw receiver 14. As the extensions 84 deflect radially outwardly at the distal end 72 when the plate screw 18 is inserted, a force will be exerted onto the inner surface of the screw receiver aperture 55 to increase by force the purchase of the screw receiver 14 on the cage 12. Also, this outward force will in turn be biased by the cage 12 back onto the plate screw 18, thereby, tightening onto the plate screw 18. This action helps to keep the screw receiver 14 secured to the cage 12 and the plate screw 18 secured inside the screw receiver 14.

Figure 19:
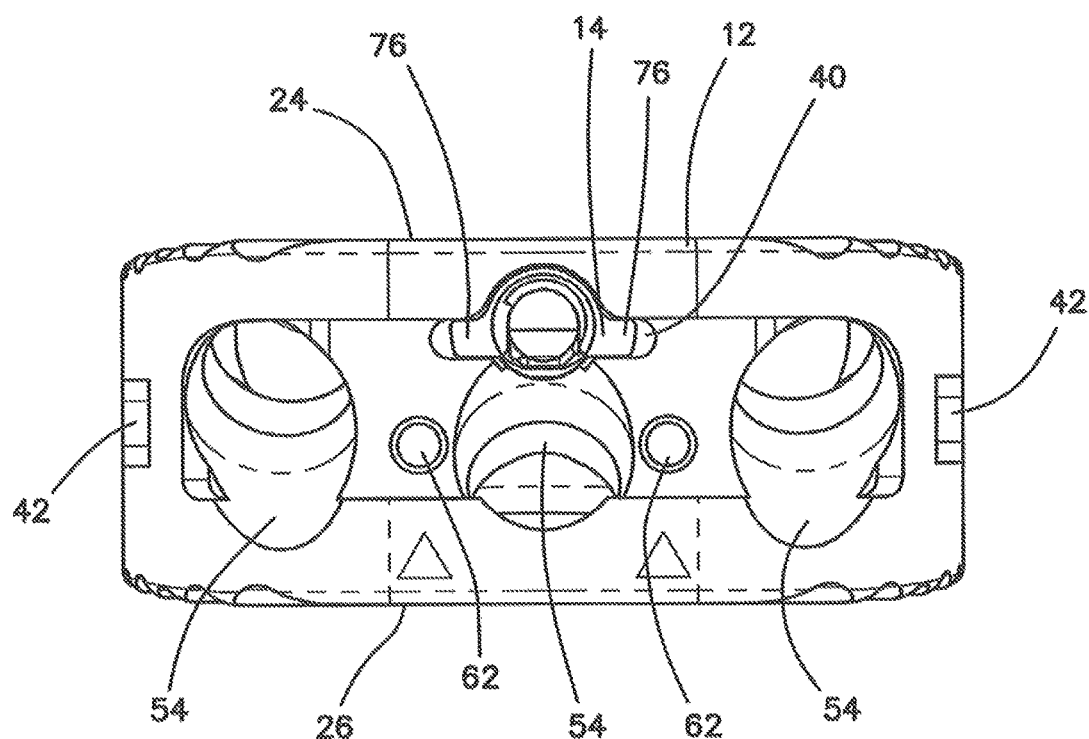
FIG. 19 is a front elevational view of cage and screw receiver according to the present invention.
Figure 20:
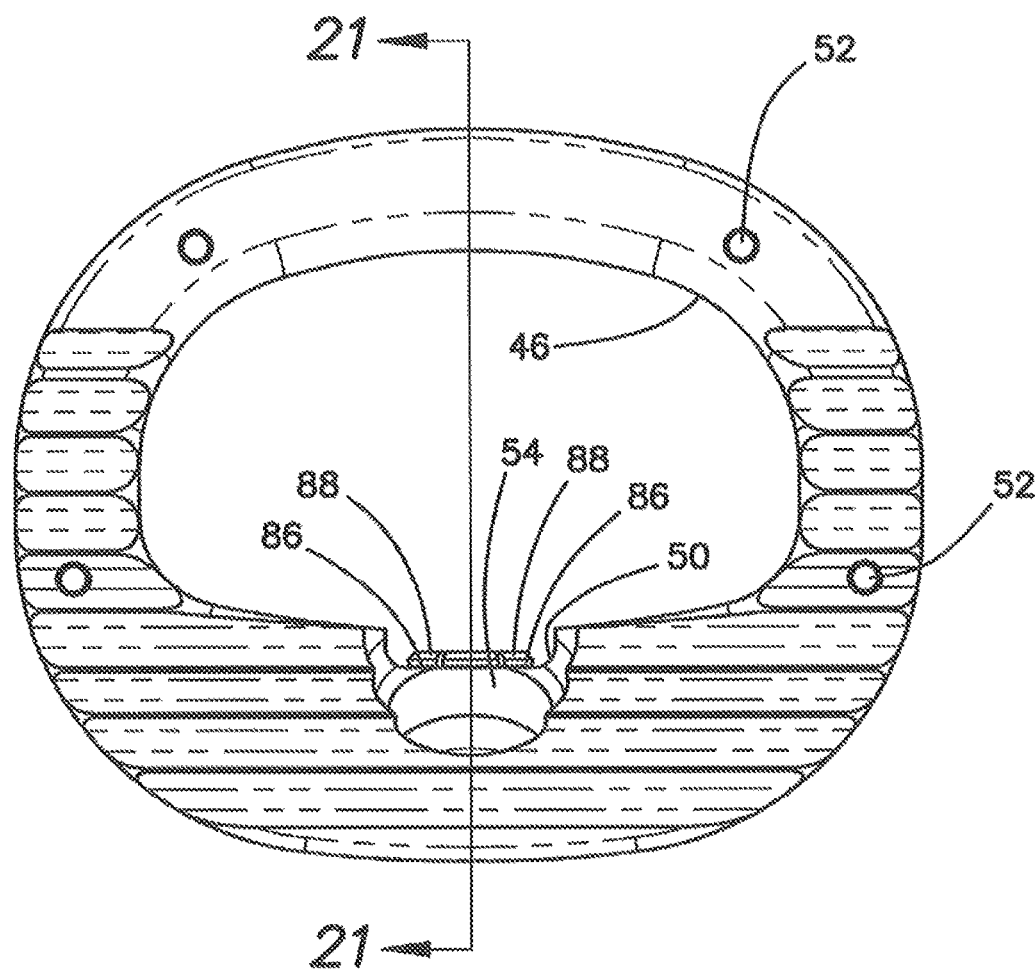
FIG. 20 is a bottom planar sectional view of a cage and screw receiver according to the present invention.
Figure 21:
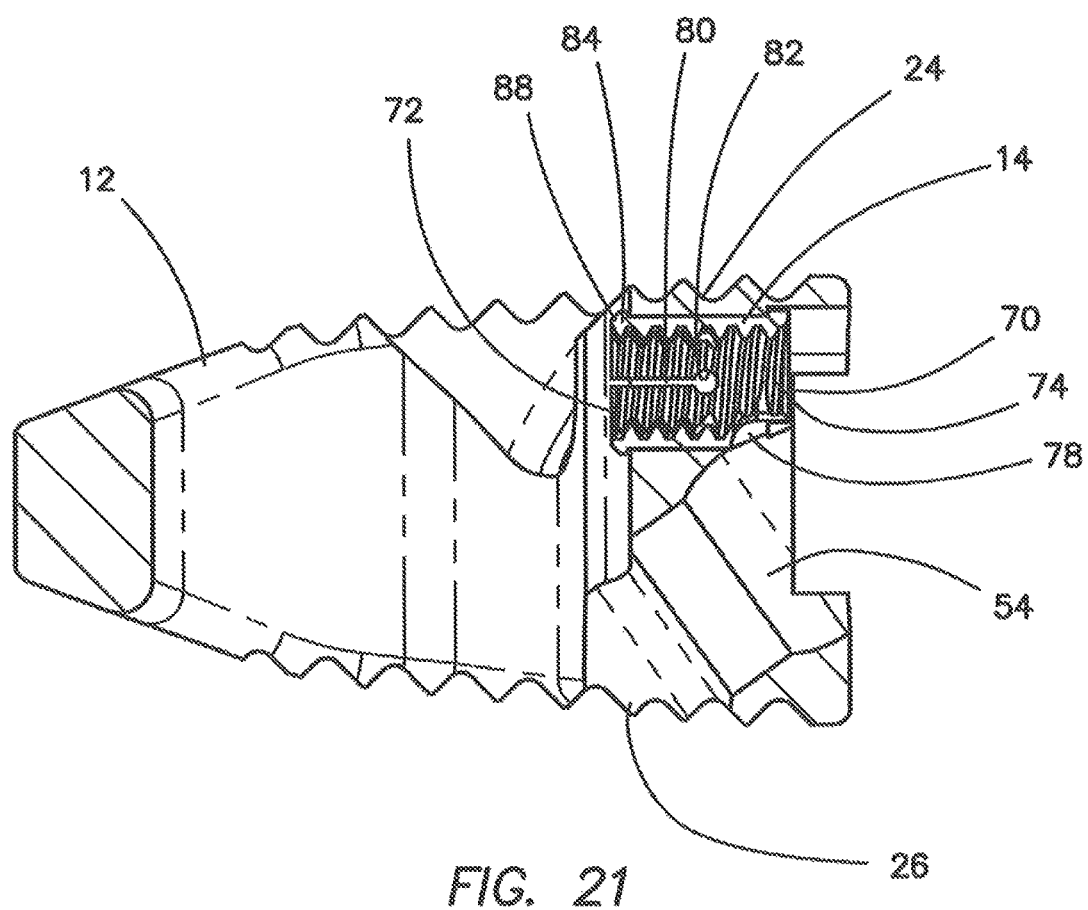
FIG. 21 is a cross-sectional view taken along line 21-21 of FIG. 20 of a cage and screw receiver according to the present invention.

The screw receiver 14 is configured to be inserted into the screw receiver aperture 55. The distal end 72 leads the insertion into the screw receiver aperture 55. The beveled surface 88 will ramp against the screw receiver aperture 55 as the screw receiver 14 is being inserted and, thereby, deflect the extensions 84 inwardly as it passes into and through the screw receiver aperture 55. At the inner surface 46 of the cage 12, the detent 86 around the circumference of the screw receiver 14 of each deflectable extension 84 will exit the screw receiver aperture 55 and snap back outwardly such that the detents 86 reside outside of the screw receiver aperture 55 at the inner surface 46 of the cage 12 in the location of the inner recess 50. The distal end 72 of the screw receiver 14 will be located within the inner recess 50 and the proximal end 70 including the wings 76 of the screw receiver 14 will be located within the screw receiver recess 44. The snapping of the extensions 84 into position locks the screw receiver 14 with respect to the cage 12 preventing its movement back out in the proximal direction and the wings 76 fix the screw receiver 14 preventing it from moving in the distal direction as the wings 76 rest in and abut the screw receiver recess 40. In another variation, the cage 12 includes an inner ridge 45 such as shown in FIG. 12 located between the sidewall 28 and the inner surface 16 of the cage 12. The inner ridge 45 is formed circumferentially in the screw receiver aperture 55. The inner ridge 45 is sized and configured to receive the detent 86 which may be formed anywhere along the screw receiver 14. The detent 86 snaps into the inner ridge 45 as the screw receiver 14 passes into the screw receiver aperture 55 to lock and retain the screw receiver 14 with respect to the cage 12 instead of snapping against the inner surface 16 of the cage 12. To remove the screw receiver 14, the finger-like extensions 84 at the distal end 72 are deflected toward the longitudinal axis of the screw receiver 14 to allow the detents 86 to move into the screw receiver aperture 55. FIGS. 19-21 illustrate the screw receiver 14 located within the screw receiver aperture 55 of the cage 12. The screw receiver 14 is made of metal and configured as described to attach to a cage 12 made of polymer. The metallic screw receiver 14 permits a metal plate screw 18 to be used to secure the cover plate 16. The metallic screw receiver 14 provides a threaded location having metal threads for receiving a metal plate screw 18. This configuration retains the plate screw more securely than the plate screw being retained in a location having polymer threads which are weaker than metal threads. Also, in one variation, the shape of the screw receiver 14 at the proximal end is not symmetric about the lateral axis which advantageously provides easy alignment between the screw receiver 14 and the cage 12 or screw receiver recess 40. Because of the non-symmetrical arrangement of the screw receiver 14 at the proximal end the scallop 78 of the screw receiver 14 is easily aligned with the scallop 59 formed at the intersection of the screw receiver aperture 55 and one of the bone screw apertures 54 permitting closer arrangement of elements and greater angulation of the bone screw 20 placed inside the intersecting bone screw aperture 54. This alignment is accomplished by the wings 76. In another variation, this alignment is provided by a screw receiver 14 having an asymmetrical shape that is aligned with a correspondingly-shaped screw receiver aperture 55 in the cage 12.

Figure 22:
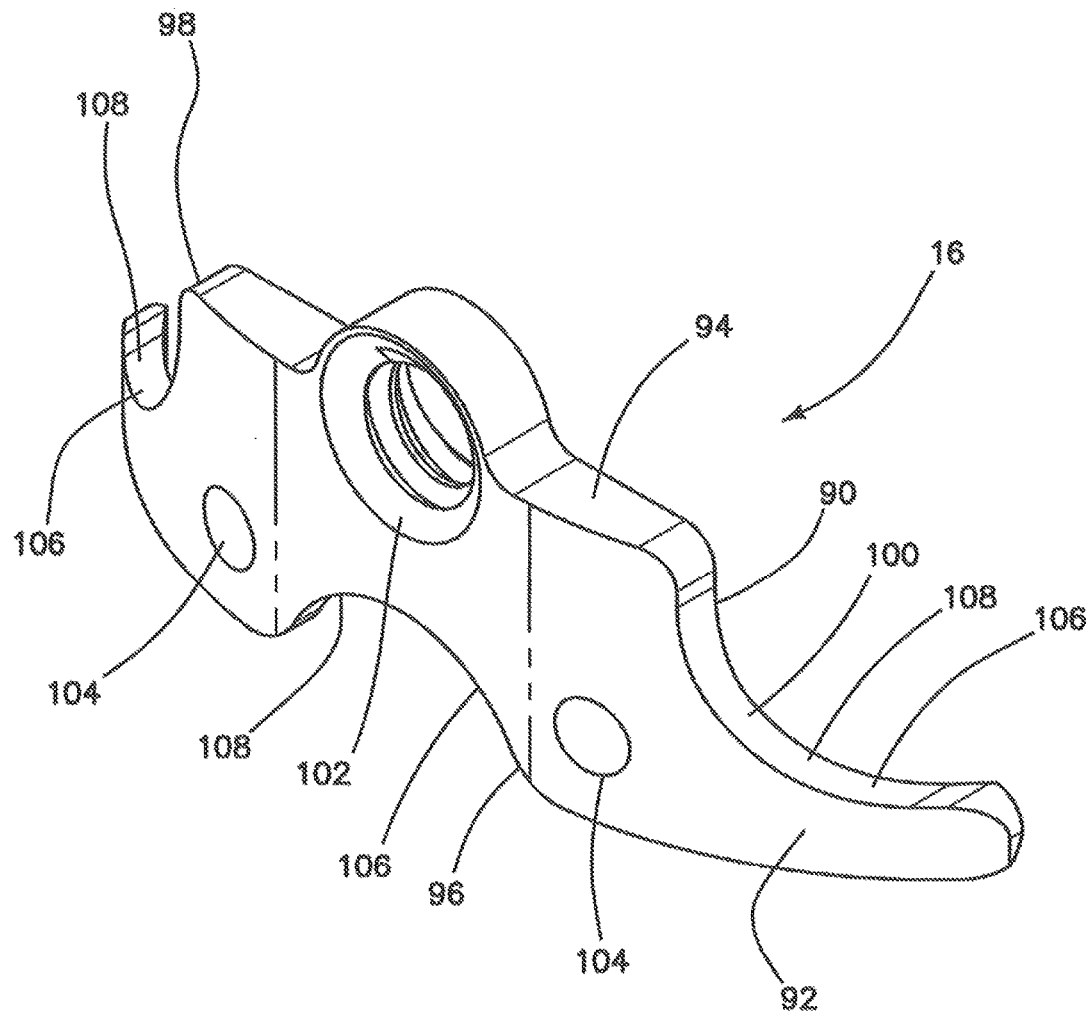
FIG. 22 is a top perspective view of a cover plate according to the present invention.
Figure 23:
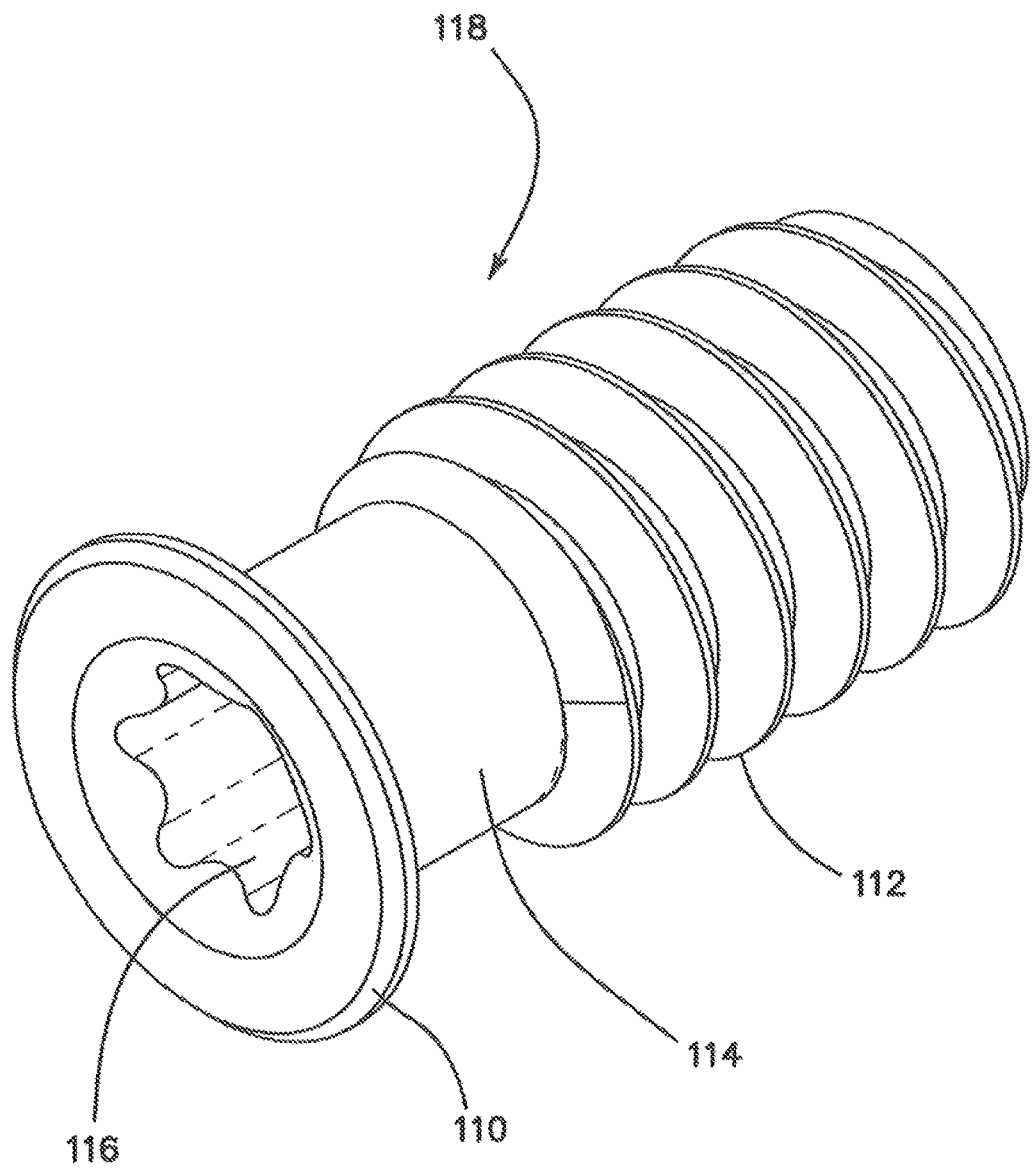
FIG. 23 is a top perspective view of a plate screw according to the present invention.
Figure 24:
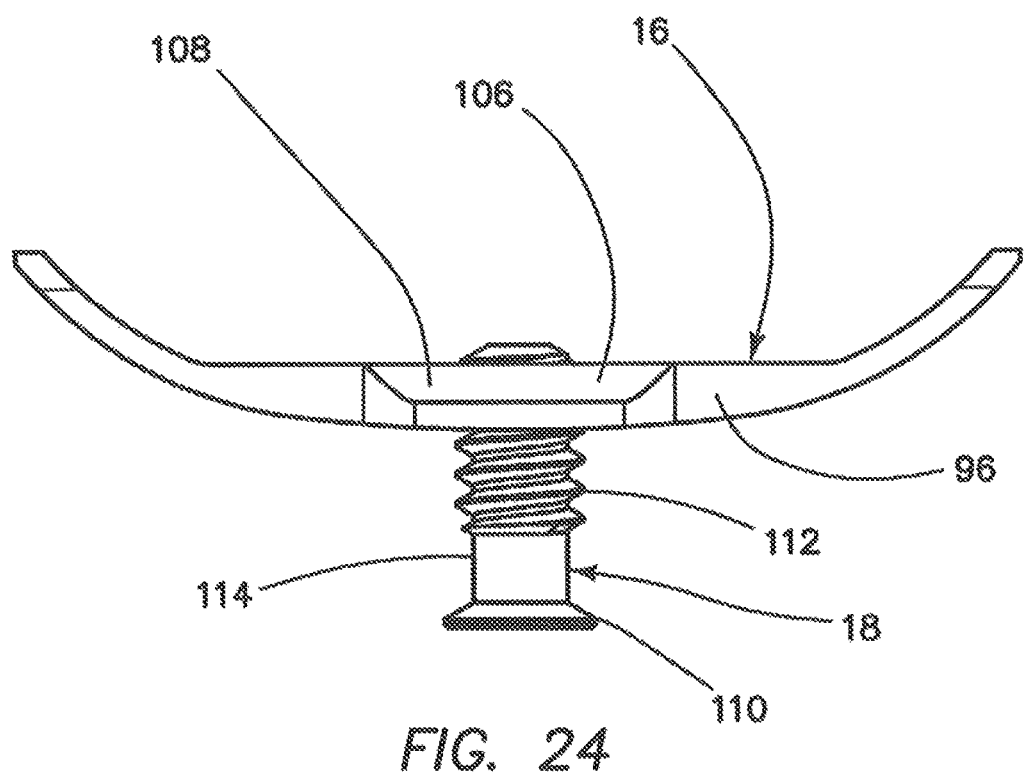
FIG. 24 is a bottom view of a cover plate and plate screw according to the present invention.

Turning now to FIGS. 22-24, the cover plate 16 and plate screw 18 will now be described in greater detail. The cover plate 16 includes an inner surface 90 and an outer surface 92 interconnected by a top end 94, bottom end 96 and a first side 98 and second side 100. The cover plate 16 is configured for attachment to the cage 12 and, in particular, for attachment to the anterior surface 30 of the cage 12. The cover plate 16 has curved contour that matches the curvature of the cage sidewall 28 and is sized and configured to fit within the cover plate recess 38 such that the outer surface 92 is flush with the outer surface of the cage 12. The cover plate 16 includes a threaded plate screw aperture 102 configured to receive a plate screw 18 to attach the cover plate 16 to the cage 12. The cover plate 16 also includes two instrument apertures 104 configured for connection with an instrument used to carry the cover plate 16 to the surgical site and attach the cover plate 16 to the cage 12. The plate screw aperture 102 is located along the midline and the instrument apertures 104 are located on either side of the midline and the plate screw aperture 102. The cover plate 16 includes one or more bone screw windows 106 that correspond to bone screw apertures 54 on the cage 12. With the cover plate 16 in position and attached to the cage 12, the bone screw windows 106 are substantially aligned with the bone screw apertures 54 and configured to cover at least partially the bone screw apertures 54 and/or cover at least partially the bone screws 20 located in the bone screw apertures 54 to prevent the bone screws 20 from backing out with respect to the cage 12. Either one or more of the top end 94, bottom end 96, first side 98 and second side 100 include bone screw windows 106 defined by cutouts 108 in the cover plate 16. The cutouts 108 form bone screw windows 106 when the cover plate 16 is attached to the cage 12. The cutouts 108 also serve to cover bone screws 20 located inside the cage 12 and prevent them from backing out. Instead of completely covering the bone screws 20, the cover plate 16 includes bone screw windows 106 in order to permit at least part of the proximal end of the bone screw 20 to protrude through the window 106 and, thereby, allow a greater degree of polyaxial angulation of the bone screw 20 relative to the cage 12. Instead of cutouts 108, the cover plate 16 may include bone screw windows formed within the cover plate 16. The cover plate 16 is typically made of biocompatible metal such as stainless, surgical steel, titanium and the like. The cover plate 16 may also be made of any other suitable material including but not limited to PEEK.

With particular reference to FIG. 23, the plate screw 18 will now be described in greater detail. The plate screw 18 includes a head 110 interconnected to a threaded shank 112 by a neck 114. The head 110 has a lateral dimension that is larger than the lateral dimension of the shank 112. At the proximal end of the head 110, a longitudinal socket 116 is formed and configured to engage with a driving tool to rotate the plate screw 18 relative to the cover plate 16. A substantially hexagonal, daisy-shaped socket 116 is shown in FIG. 23; however, the socket 116 can be of any shape that allows an instrument to rotate the plate screw 18. The shank 112 is sized and configured to thread into the plate screw aperture 102 in the cover plate 16 until the head 110 abuts the cover plate 16.

Figure 25:
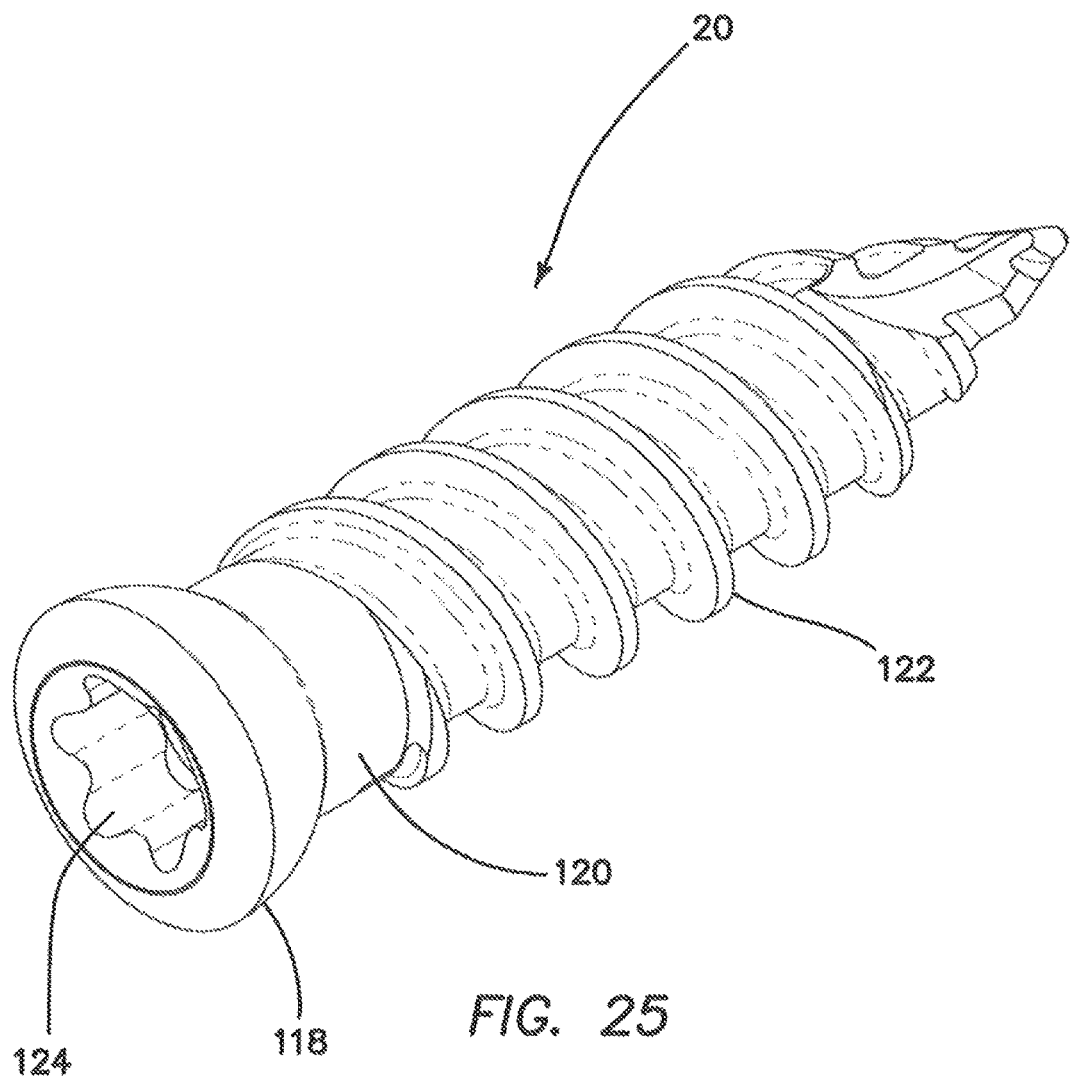
FIG. 25 is a top perspective view of a bone screw according to the present invention.

Turning to FIG. 25, the bone screw 20 will be now described in greater detail. The bone screw 20 is an exemplary orthopedic fastener that is preferably used with the interbody spacer 10 of the present invention although other types of fasteners may be employed. The bone screw 20 includes a screw head 118, neck 120 and threaded shank 122. The head 118 is bulbous having a larger lateral dimension than the threaded shank 122. Also, the outer surface of the head 118 is curved, spherical in shape or partially spherical or a frustum or frusta of a sphere having a region of a sphere delimited by one plane parallel to a plane containing a diameter or having a region of a sphere delimited by two planes which in one variation may be parallel to each other. The proximal plane of the frusta-spherical head 118 includes an opening that serves as an instrument recess or socket 124 configured to engage a complementary tip of a surgical tool for driving the bone screw into bone. A substantially hexagonal, daisy-shaped recess 124 is shown in FIG. 25; however, the recess 124 can be of any shape that allows a surgical tool to drive the bone screws 20 into the vertebral column. The head 118 of the bone screw 20 corresponds to the shape of the bone screw apertures 54 in the cage 12. The bone screws 20 are configured to allow polyaxial, variable angle or fixed angled orientation with respect to the cage 12 while disposed inside the bone screw apertures 54. The angulation of the bone screws 20 with respect to the cage 12 allows a desired angle or orientation with respect to the cage 12 and adjacent vertebral bodies to be achieved to anchor the cage 12 to the vertebrae. The bone screws 20 are preferably self-tapping and configured for insertion into bony material, however, other screws requiring holes to be drilled or pre-tapped can also be employed.

Figure 26:
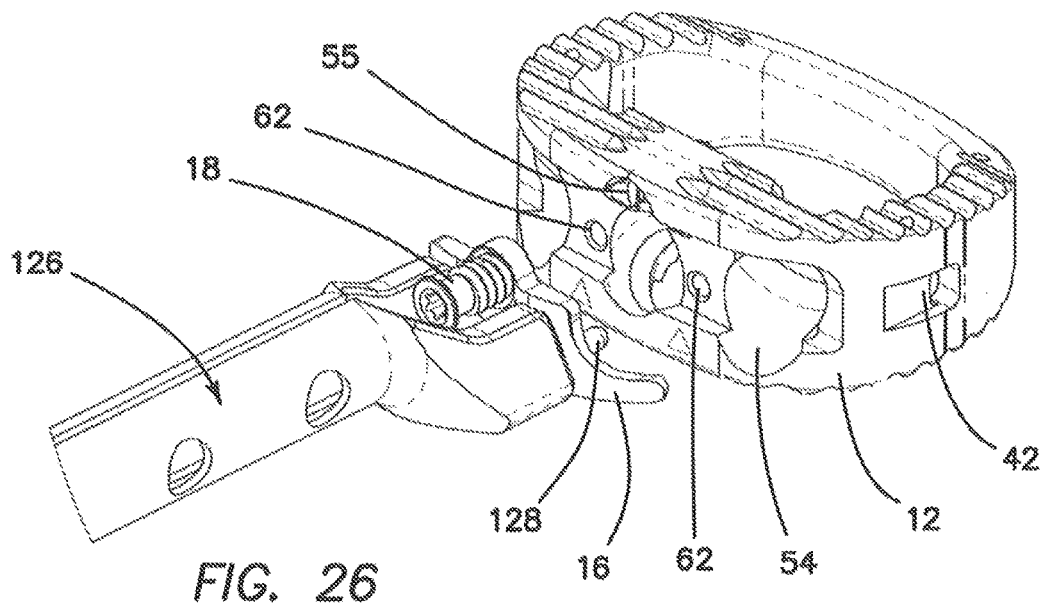
FIG. 26 is a top perspective view of an instrument attached to a cover plate and a cage according to the present invention.
Figure 27:
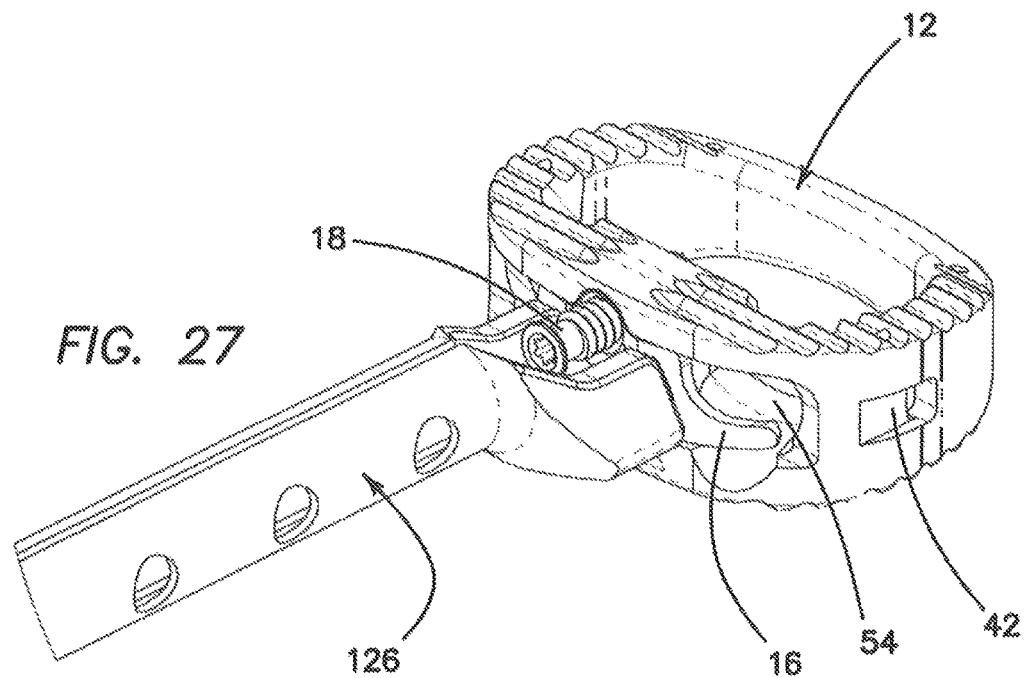
FIG. 27 is a top perspective view of an instrument attached to a cover plate and a cage according to the present invention.

In use, the present interbody spacer 10 is configured for use as an ALIF cage in spinal surgical procedures. It is understood that novel features of the present invention can find application in different types of cages including but not limited to interbody spacers for PLIF, TLIF, XLIF surgical procedures as well as other types of orthopedic implants. Implanting the interbody spacer 10 involves removal, in whole or in part, of the disc material from the intervertebral space at the target vertebral level where the interbody spacer 10 will be implanted. The patient is oriented to provide some distraction of the disc space and to provide access to the anterior of the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration. A surgeon will then select an appropriately sized cage 12 that has the best size in footprint and height and lordotic angle for the target space. The surgeon may use an insertion instrument to grasp the cage 12 and place it at the mouth of the intervertebral space and move and orientate the cage 12 into its proper orientation within the intervertebral space. The insertion instrument typically has two distal prongs configured to securely attach to the cage 12 at the instrument notches 42. The surgeon may determine the position of the cage 12 with the help of one or more x-ray fluoroshots. Since the position of the radiographic markers 22 are known relative to the cage 12, a surgeon can determine the position of the cage 12 in the target space by viewing the positions of the radiographic markers 22 embedded inside the radiographic pin holes 52 that appear in the x-ray and reposition the cage 12 as needed until final placement is achieved. The cage 12 may include bone graft or other material located inside the central opening 44 of the cage 12 to promote ingrowth and blood supply in order to grow active and live bone from the adjacent spinal vertebrae to inter-knit with the spacer 10 and, thereby, eventually immobilize and fuse the adjunct spinal vertebrae. The cage 12 is placed such that the anterior surface 30 of the cage 12 faces the anterior side of the patient and the top surface 24 contacts the lower endplate of the upper vertebral body and the bottom surface 26 of the cage 12 contacts the upper endplate of the lower vertebral body on either side of the target intervertebral space. The geometry of the ridges 48 on the top surface 24 and the bottom surface 26 provide resistance to migration of the cage 12 while inside the target space. Other coatings and surface textures may also be provided on the cage 12. Next, bone screws 20 are deployed via a surgical instrument such as a bone screw driver. The bone screws 20 are inserted into the bone screw apertures 54 and tapped into the bone of the adjoining vertebral bodies. The one or more bone screws 20 are passed through the cage 12 via the bone screw apertures 54 in a trajectory transverse to the longitudinal axis and into the upper and lower vertebral bones. As the bone screws 20 are tightened, the vertebral bodies penetrated with the bone screws 20 will compress onto both sides of the load-bearing cage 12 and provide pressure to help facilitate fusion. Additional bone graft material may be placed in the intervertebral disc space. Next, with reference to FIGS. 26 and 27, an insertion instrument 126 is provided that includes an elongate shaft having a two pins 128 at the its distal end. The pins 128 are sized and configured for insertion through the instrument apertures 104 on the cover plate 16. The plate screw 18 is partially inserted into the plate screw aperture 102 and the cover plate 16 is mounted onto the pins 128 of the insertion instrument 126. The cover plate 16 and plate screw 18 are delivered to the anterior surface 30 of the cage 12 and the protruding instrument pins 128 are aligned with and inserted into the guide apertures 62 of the cage 12 placing the plate screw 18 into alignment with the lumen 68 of the screw receiver 14. The plate screw 18 is threadingly engaged with the threads 74 on the screw receiver 14 and threaded with a driver into the screw receiver 14. As the plate screw 18 is driven, the wings 76 on the screw receiver 14 counter the torque on the plate screw 18 as they abut the sides of the screw receiver recess 14 when the plate screw 18 is rotated into threaded engagement by the driver. The wings 76 abutting the screw receiver recess 14 advantageously provide an anti-rotation mechanism of the screw receiver 14 with respect to the cage 12. Without this anti-rotation mechanism, the plate screw 18 and screw receiver 14 would rotate together and the plate screw 18 would not move with respect to the screw receiver 14. This anti-rotation mechanism may also be provided by an asymmetrically-shaped screw receiver 14. As the plate screw 18 moves distally into the screw receiver 14, the distal finger-like extensions 84 of the screw receiver 14 begin to expand because the lumen 68 of the screw receiver 14 narrows toward the distal end when in its normal undeflected orientation. The plate screw 18 deflects the extensions 84 outwardly when the plate screw 18 is threaded distally into the screw receiver 14. The deflected extensions 84 in turn exert a greater force onto and creating more friction with respect to the cage 12 which biases tightly onto the plate screw 18. This action and deflected configuration of the extensions 84 help to further secure the screw receiver 14 with respect to the cage 12 and in turn secure the cover plate 16 with respect to the cage 12 and, thereby, provide a stronger and more secure anti-backout mechanism to prevent the bone screws 20 from loosening and/or exiting the cage 12. With the plate screw 18 in place, the cover plate 16 resides inside the cover plate recess 38. The cover plate 16 is disposed over a head 118 of at least one of the plurality of bone screws 20 implanted together with the cage 12. The cover plate 16 is held in place over one of the plurality of bone screws 20 using a metallic plate screw 18 securely threaded into a metallic screw receiver 14 that is securely connected to the cage 12 made of polymer. No secondary fixation is required for connecting the metallic screw receiver 14 into the plastic cage 12, that is, there is no need to have a second component to hold the screw receiver 14 fixed with respect to the cage 12. The cover plate 16 serves as a locking plate and provides anti-back-out protection for the bone screws 12. When actuated, the plate screw 18 compresses the cover plate 16 against the body structure of the cage 12. The cover plate 16 locks the bone screws 20 into the cage and vertebral bodies and prevents them from loosening and backing out. In one variation, because the bone screws 20 are partially covered, the bone screws are permitted to angulate at a greater angle and protrude in part through the bone screw windows 106. The protrusion of the heads 118 of bone screws 20 through the bone screw windows 106 is visible in FIGS. 5-6. The bone screws 20 are shown at a given angle although any suitable angle(s) for a given application may be utilized and as may any suitable number of screws. Additional instrumentation such as rods or screws may also be used to further stabilize the spine across the target level. Any of the components in the present invention are manufactured from metal such as titanium, ceramic, plastic such as PEEK and carbon fiber reinforced polymer, biomaterial including but not limited to any of a number of biocompatible implantable polymers including PEKK, PEKEK, polyetheretherketone (PEEK) being preferred, titanium ceramic, bone or other material etc. The present invention can be employed and is suitable for use where ever the backing out of screws is to be prevented and anywhere along the spine including but not limited to cervical, thoracic, lumbar or sacral or between other bony structures outside of the spinal region. Embodiments of the present invention are standalone interbody devices which may be designed in the general style of an ALIF device, TLIF device, PLIF device or other device. In addition, the size and/or shape of the basic embodiments disclosed herein may be adapted by one skilled in the art for use in various levels of the spine, namely the cervical spine, thoracic spine and the lumbar spine. Thus while various embodiments herein may be described by way of example with respect to the lumbar spine such disclosures apply with equal weight to the other levels of the spine.

It is understood that various modifications may be made to the embodiments of the interbody spacer disclosed herein. Therefore, the above description should not be construed as limiting, but merely as exemplifications of preferred embodiments. Those skilled in the art will envision other modifications within the scope and spirit of the present disclosure.

We claim:

1. An interbody spacer for a spine, comprising:
   a monolithic cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture having a smooth surface; the screw receiver aperture being sized and configured to receive a screw receiver;
   a screw receiver connected to the cage and located inside the screw receiver aperture; the screw receiver having a longitudinal axis, a smooth outer surface and a threaded lumen extending between a proximal end and a distal end along the longitudinal axis of the screw receiver;
   a plate screw having a proximal end and a threaded shank; the plate screw being sized and configured for being threadingly and removably received inside the threaded lumen of the screw receiver;
   a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and
   a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out.

2. The interbody spacer of claim 1 wherein the cover plate includes at least one bone screw window configured to permit the head of at least one of the plurality of bone screws to protrude past the sidewall of the cage when angulated with respect to the cage.

3. The interbody spacer of claim 1 wherein the screw receiver is made of metal and the cage is made of polymer and the plate screw is made of metal.

4. An interbody spacer for a spine, comprising:
a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;
a screw receiver connected to the cage and located inside the screw receiver aperture; the screw receiver having a longitudinal axis and a threaded lumen extending between a proximal end and a distal end along the longitudinal axis of the screw receiver;
a plate screw having a proximal end and a threaded shank; the plate screw being sized and configured for being threadingly and removably received inside the threaded lumen of the screw receiver;
a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and
a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;
wherein the cover plate is disposed over the head of at least one of the plurality of bone screws when attached to the cage to retain the bone screw and prevent the bone screw from backing out;
wherein the screw receiver has a longitudinal axis extending from the proximal end to the distal end of the screw receiver; the screw receiver having a scallop opening at the proximal end and extending longitudinally toward the distal end;
wherein the screw receiver aperture intersects with one of the bone screw apertures to form a scallop-shaped intersection; the screw receiver being disposed inside the cage such that the scallop-shaped intersection is aligned with the scallop of the screw receiver.

5. The interbody spacer of claim 4 wherein the screw receiver includes one or more wings extending transverse to the longitudinal axis of the screw receiver;
wherein the cage includes a screw receiver recess sized and configured to receive the one or more wings and align of scallop of the screw receiver with the scallop-shaped intersection.

6. The interbody spacer of claim 1 wherein the cage includes a cover plate recess formed in the sidewall; the cover plate recess being sized and configured to recess the cover plate with respect to the sidewall.

7. The interbody spacer of claim 1 further including a cover plate recess formed in the sidewall of the cage and configured to recess the cover plate and a screw receiver recess located within the cover plate recess; the screw receiver recess being configured to recess the screw receiver with respect to the cover plate recess.

8. The interbody spacer of claim 1 wherein the bone screw apertures are formed in an anterior surface of the sidewall.

9. The interbody spacer of claim 1 wherein the screw receiver has an asymmetrical outer surface configured to align within a correspondingly-shaped screw receiver aperture.

10. An interbody spacer for a spine, comprising:
a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;
a screw receiver connected to the cage and located inside the screw receiver aperture; the screw receiver having a threaded lumen extending between a proximal end and a distal end; the screw receiver having a plurality of slits extend from the distal end toward the proximal end that divide the distal end of the screw receiver into a plurality of deflectable extensions;
a plate screw having a proximal end and a threaded shank; the plate screw being sized and configured for being threadingly and removably received inside the threaded lumen of the screw receiver;
a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and
a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;
wherein the cover plate is disposed over the head of at least one of the plurality of bone screws when attached to the cage to retain the bone screw and prevent the bone screw from backing out; and
wherein the screw receiver is connected to the cage such that the distal end of the screw receiver is distal to the inner surface of the cage.

11. An interbody spacer for a spine, comprising:
a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;
a screw receiver connected to the cage and located inside the screw receiver aperture; the screw receiver having a threaded lumen extending between a proximal end and a distal end; the screw receiver having a plurality of slits extend from the distal end toward the proximal end that divide the distal end of the screw receiver into a plurality of deflectable extensions;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out;

wherein the lumen of the screw receiver decreases in size toward the distal end; the screw receiver being configured such that threading the plate screw into the decreasing lumen will deflect the extensions laterally outwardly into frictional engagement with the cage to retain the screw receiver to the cage.

12. An interbody spacer for a spine, comprising:

a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;

a screw receiver connected to the cage and located inside the screw receiver aperture; the screw receiver having a threaded lumen extending between a proximal end and a distal end; the screw receiver having a plurality of slits extend from the distal end toward the proximal end that divide the distal end of the screw receiver into a plurality of deflectable extensions;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out;

wherein the lumen of the screw receiver has an inner diameter that progressively decreases with distance toward the distal end of the screw receiver.

13. An interbody spacer for a spine, comprising:

a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;

a screw receiver connected to the cage and located inside the screw receiver aperture; the screw receiver having a threaded lumen extending between a proximal end and a distal end; the screw receiver having a plurality of slits extend from the distal end toward the proximal end that divide the distal end of the screw receiver into a plurality of deflectable extensions;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out;

wherein the screw receiver aperture extends between the sidewall and inner surface; and the screw receiver has an outwardly extending detent; the detent residing against the inner surface of the cage when connected to the cage; the detent being configured to prevent the screw receiver from backing out of the cage.

14. The interbody spacer of claim 10 wherein the screw receiver has an outwardly extending detent and the cage includes an inner ridge in the location of the screw receiver aperture; the detent residing against the inner ridge when connected to the cage; the detent being configured to prevent the screw receiver from moving proximally within the cage.

15. An interbody spacer for a spine, comprising:

a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;

a screw receiver having a proximal end and a distal end connected to the cage and located inside the screw receiver aperture; the screw receiver having a threaded lumen along a longitudinal axis; the screw receiver including one or more wings extending transverse to the longitudinal axis at the proximal end; and the screw receiver having an outwardly extending detent at the distal end;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out.

16. The interbody spacer of claim 15 wherein the sidewall of the cage includes a screw receiver recess sized and configured to recess the one or more wings.

17. An interbody spacer for a spine, comprising:
a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;

a screw receiver connected to the cage and located inside the screw receiver aperture; the screw receiver having a threaded lumen along a longitudinal axis; the screw receiver including one or more wings extending transverse to the longitudinal axis;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out; and wherein the sidewall of the cage includes a screw receiver recess configured to prevent the screw receiver from rotating relative to the cage.

18. The interbody spacer of claim 15 further including a cover plate recess formed in the sidewall to recess the cover plate and a screw receiver recess sized and configured to recess the wings; the screw receiver recess being formed inside the plate recess to recess the wings relative to the plate recess.

19. An interbody spacer for a spine, comprising:
a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;

a screw receiver connected to the cage and located inside the screw receiver aperture; the screw receiver having a threaded lumen along a longitudinal axis; the screw receiver including one or more wings extending transverse to the longitudinal axis;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out; and wherein the screw receiver aperture extends between the sidewall and inner surface of the cage.

20. An interbody spacer for a spine, comprising:
a cage having a top surface and a bottom surface interconnected by a sidewall; the cage includes a central opening extending between the top surface and the bottom surface and defining an inner surface; the cage includes a plurality of bone screw apertures opening in the sidewall; the cage includes a screw receiver aperture; the screw receiver aperture being sized and configured to receive a screw receiver;

a screw receiver connected to the cage and located inside the screw receiver aperture; the screw receiver having a threaded lumen along a longitudinal axis; the screw receiver including one or more wings extending transverse to the longitudinal axis;

a plate screw having a proximal end and a threaded shank; the plate screw being sized and configured for being threadingly and removably received inside the threaded lumen of the screw receiver;

a cover plate having an inner surface and an outer surface and a plate screw aperture extending between the inner surface and the outer surface; the cover plate being removably connected to the sidewall of the cage with the plate screw inserted into the plate screw aperture and threaded into the lumen of the screw receiver; and a plurality of bone screws disposed inside the plurality of bone screw apertures; each bone screw having a head at a proximal end and a threaded shank extending toward a distal end for anchoring into bone; the plurality of bone screws being configured to secure the interbody spacer between two bony components of the spine;

wherein the cover plate is disposed over the head of at least one of the plurality of bone screws when attached to the cage to retain the bone screw and prevent the bone screw from backing out;

wherein the screw receiver has a scallop opening at the proximal end and extending longitudinally toward the distal end;

wherein the screw receiver aperture intersects with one of the bone screw apertures to form a scallop-shaped intersection; the screw receiver being disposed inside the cage such that the one or more wings align the scallop of the screw receiver with the scallop-shaped intersection.

* * * * *